(12) United States Patent
Ahmed et al.

(10) Patent No.: US 10,829,509 B2
(45) Date of Patent: Nov. 10, 2020

(54) PURE HEPTASULFATED DISACCHARIDES HAVING IMPROVED ORAL BIOAVAILABILITY

(71) Applicant: OPKO Pharmaceuticals, LLC., Miami, FL (US)

(72) Inventors: Tahir Ahmed, Coral Gables, FL (US); Arie Gutman, Nesher (IL); Irina Fedotev, Haifa (IL); Igor Rukhman, Yokneam Illit (IL); Olga Grossman, Kibbutz Adamit (IL)

(73) Assignee: OPKO Pharmaceuticals, LLC, Miami, FL (US)

( * ) Notice: Subject to any disclaimer, the term of this patent is extended or adjusted under 35 U.S.C. 154(b) by 0 days.

(21) Appl. No.: 16/325,940

(22) PCT Filed: Aug. 14, 2017

(86) PCT No.: PCT/US2017/046774
§ 371 (c)(1),
(2) Date: Feb. 15, 2019

(87) PCT Pub. No.: WO2018/035050
PCT Pub. Date: Feb. 22, 2018

(65) Prior Publication Data
US 2019/0185503 A1    Jun. 20, 2019

Related U.S. Application Data

(60) Provisional application No. 62/375,528, filed on Aug. 16, 2016.

(51) Int. Cl.
| C07H 11/00 | (2006.01) |
| C07H 1/00 | (2006.01) |
| A61K 9/00 | (2006.01) |
| A61K 31/7024 | (2006.01) |
| A61P 37/08 | (2006.01) |

(52) U.S. Cl.
CPC .............. *C07H 11/00* (2013.01); *A61K 9/007* (2013.01); *A61K 9/0019* (2013.01); *A61K 9/0053* (2013.01); *A61K 9/0073* (2013.01); *A61K 31/7024* (2013.01); *A61P 37/08* (2018.01); *C07H 1/00* (2013.01); *A61K 9/0095* (2013.01); *C07B 2200/13* (2013.01)

(58) Field of Classification Search
CPC ..... C07H 11/00; A61K 9/0019; A61K 9/0053
See application file for complete search history.

(56) References Cited

U.S. PATENT DOCUMENTS

| 5,690,910 A | 11/1997 | Ahmed et al. | |
| 5,767,104 A * | 6/1998 | Bar-Shalom | A61K 8/02 514/23 |
| 6,193,957 B1 | 2/2001 | Ahmed | |
| 6,551,616 B1 | 4/2003 | Notario et al. | |
| 7,056,898 B2 | 6/2006 | Ahmed et al. | |
| 2008/0249165 A1 * | 10/2008 | Kuszmann | C07H 3/10 514/460 |
| 2011/0136757 A1 | 6/2011 | Ahmed | |

FOREIGN PATENT DOCUMENTS

| WO | 2005/075490 A2 | 8/2005 |
| WO | 2006/017726 A2 | 2/2006 |
| WO | 2006/017727 A2 | 2/2006 |
| WO | 2006/017752 A2 | 2/2006 |

OTHER PUBLICATIONS

Ahmed, T., et al., "Effects of Inhaled Heparin on Immunologic and Nonimmunologic Bronchoconstrictor Responses in Sheep", American Review of Respiratory Disease, vol. 145, pp. 566-570, (1992).
Ahmed, T., et al., "Inhibition of Allergic Late Airway Responses by Inhaled Heparin-Derived Oligosaccharides", Journal of Applied Physiology, vol. 88, pp. 1721-1729, (2000).
Ahmed, T., et al., "Preventing Bronchoconstriction in Exercise-Induced Asthma with Inhaled Heparin", The New England Journal of Medicine, vol. 329, No. 2, pp. 09-95, (1993).
Ahmed, T., et al., "Prevention of Exercise-Induced Bronchoconstriction by Inhaled Low-Molecular-Weight Heparin", American Journal of Respiratory and Critical Care Medicine, vol. 160, pp. 576-581, (1999).
Boyle, J., "Macrophage Activation in Atherosclerosis: Pathogenesis and Pharmacology of Plaque Rupture", Current Vascular Pharmacology, vol. 3, pp. 63-68, (2005).
Campo, C., et al., "Molecular-Weight-Dependent Effects of Nonanticoagulant Heparins on Allergic Airway Responses", The American Physiological Society, vol. 86, No. 2, pp. 549-557, (1999).
Curtis, L., "Reversing Atherosclerosis?", The New England Journal of Medicine, vol. 360, No. 11, pp. 1144-1146, (2009).
Doung, M., et al., "The Effect of IVX-0142, a Heparin-Derived Hypersulfated Disaccharide, on the Allergic Airway Responses in Asthma", Allergy, vol. 63, pp. 1195-1201, (2008).
Martinez-Salas, J., et al., "Inhibition of Allergic Airway Responses by Inhaled Low-Molecular-Weight Heparins: Molecular-Weight Dependence", Journal of Applied Physiology, vol. 84, No. 1, pp. 222-228, (1998).
Pashkow, F., et al., "Astaxanthin: A Novel Potential Treatment for Oxidative Stress and Inflammation in Cardiovascular Disease", The American Journal of Cardiology, vol. 101, pp. 58D-68D, (2008).
PCT International Search Report and Written Opinion dated Jan. 24, 2011.

\* cited by examiner

*Primary Examiner* — Pancham Bakshi
(74) *Attorney, Agent, or Firm* — OPKO Pharmaceuticals, LLC; Monte R. Browder

(57) ABSTRACT

Hypersulfated disaccharides with utility in asthma or asthma related disorders are disclosed. The heptasulfated disaccharides administered orally have comparable bioavailability to the intravenous administered dosage form.

4 Claims, 10 Drawing Sheets

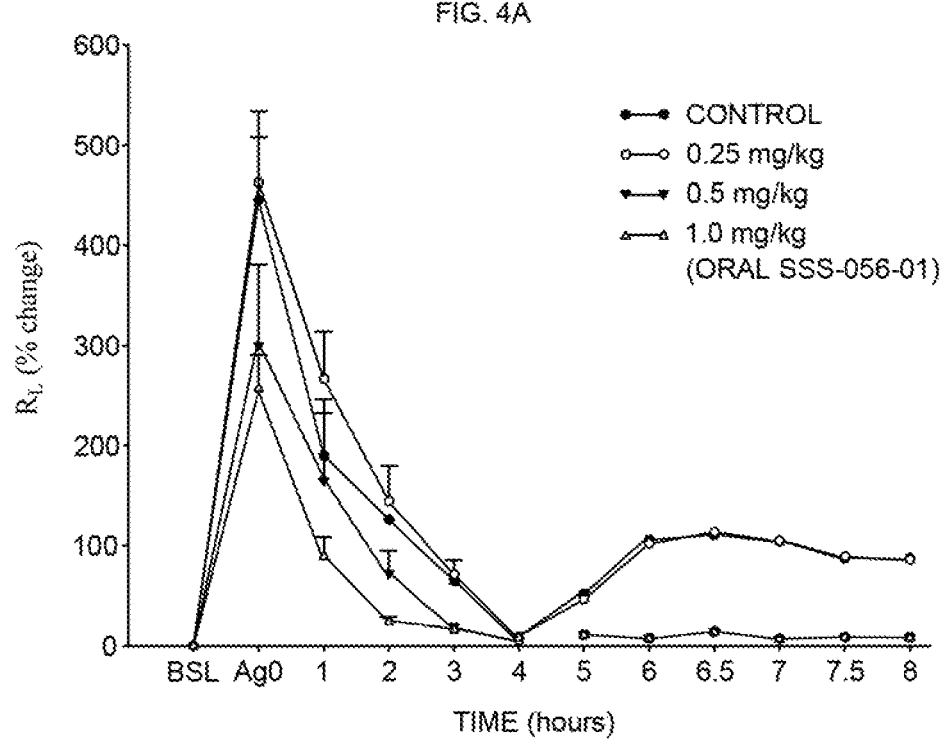
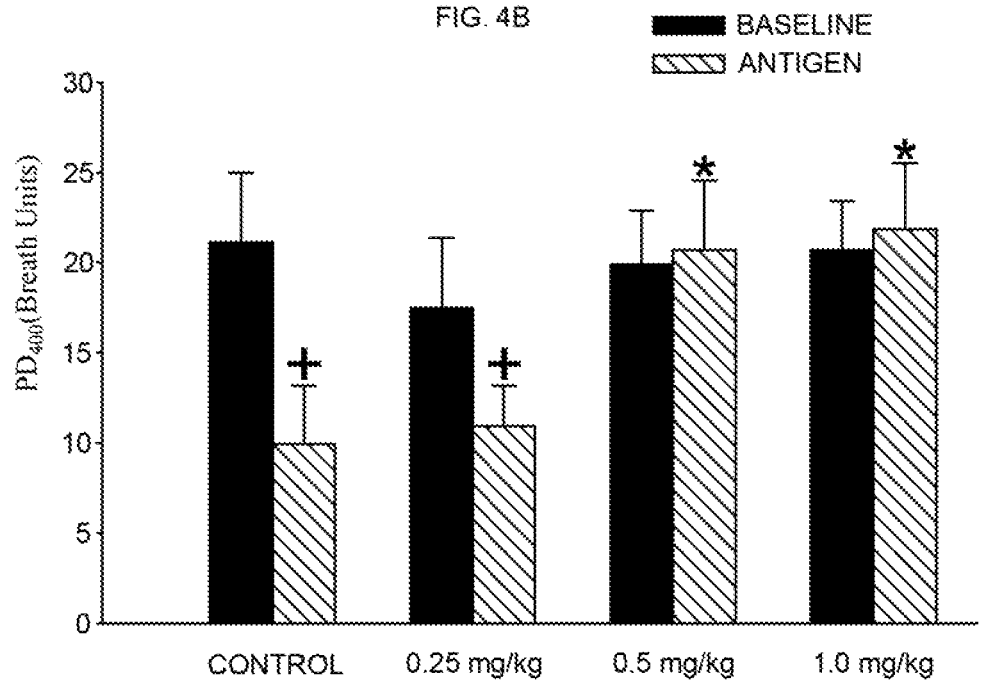

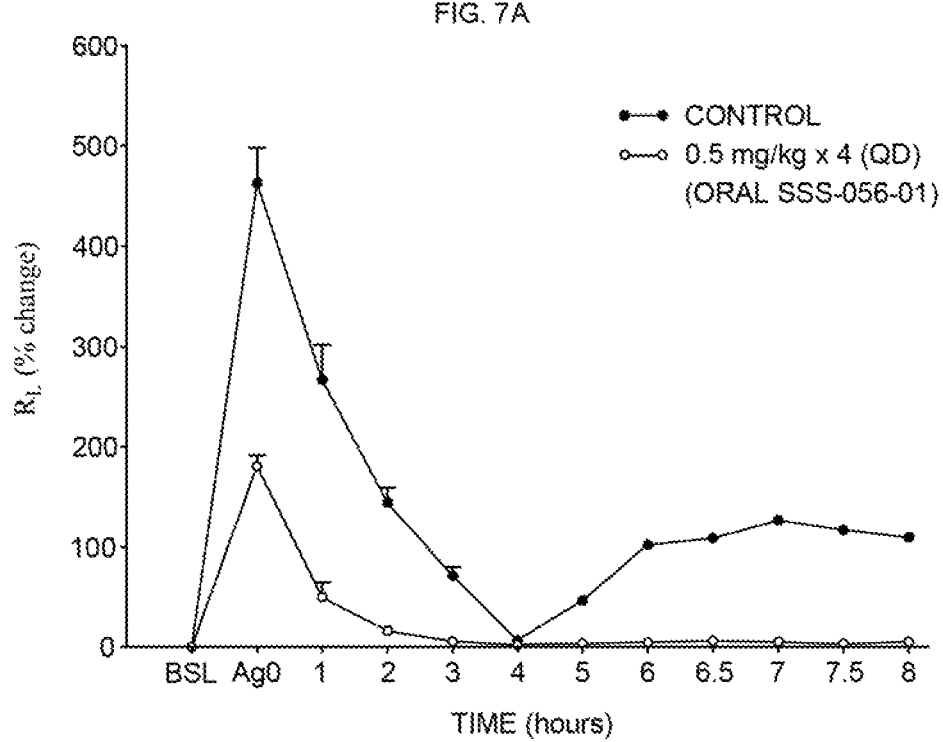
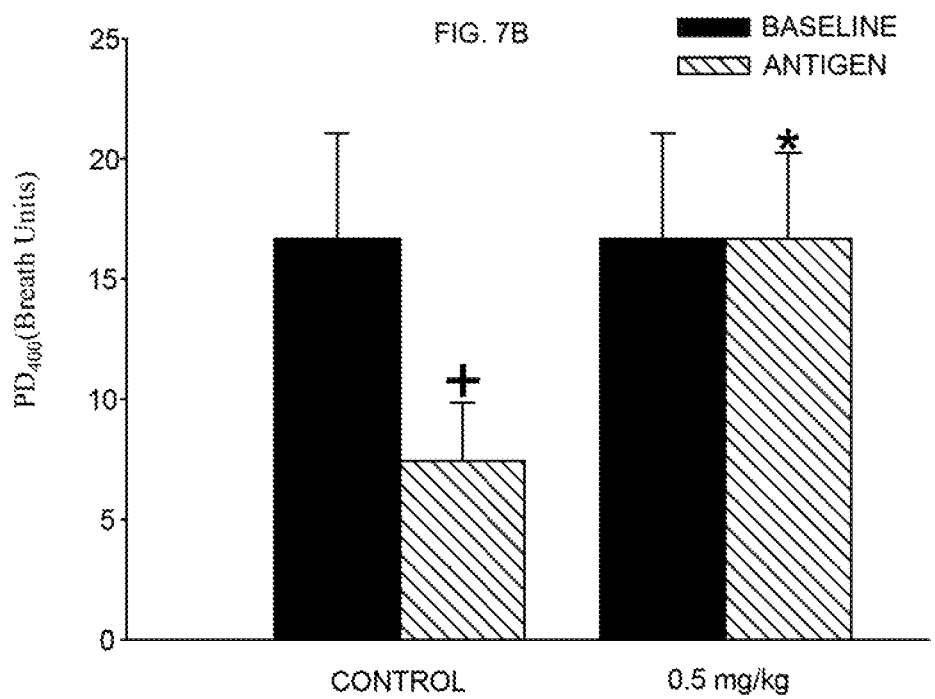

PURE HEPTASULFATED DISACCHARIDES HAVING IMPROVED ORAL BIOAVAILABILITY

FIELD OF THE INVENTION

The present invention relates to substantially pure heptasulfated disaccharide compounds of formula I and pharmaceutically acceptable salts thereof and their use in the treatment of pulmonary disease and other inflammatory conditions. The purified compounds are particularly useful in the treatment of a variety of inflammatory disorders and diseases in animals and people, and, in particular, pulmonary disorders selected from asthma and other conditions or diseases associated with inflammation of the lungs and airway.

BACKGROUND OF THE INVENTION

U.S. Pat. No. 7,056,898 (the '898 patent) discloses and claims certain hypersulfated disaccharides and methods of using same to treat certain inflammatory disorders. This patent specifically describes the use of the compounds to treat pulmonary inflammation including asthma and asthma-related pathologies, such as allergic reactions or an inflammatory disease or condition. The compounds disclosed therein are described as being capable of preventing, reversing and/or alleviating the symptoms of asthma and asthma-related pathologies, particularly the late phase response in asthma patients following antigen stimulation. The examples and figures shown therein specifically relate to intravenous and inhalation means of administration of the recited disaccharides. In the '898 patent there is a general disclosure of the oral administration of a hexasulfated disaccharide designated as 811-25-1 at a dose of 0.5 mgs/kg to sheep, but no specific data is shown. There is also no disclosure therein of any specific oral formulation nor any specific disclosure of any data related to administration of a specific oral formulation. Additional patents have been published or granted that claim the compounds disclosed in the '898 patent along with polymers that are used to enhance the low bioavailability of the hexasulfated discaccharides disclosed in the '898 patent-see U.S. Pat. No. 8,546,351. In fact, the delivery enhancing polymers such as Carbopol® are described in the '351 patent as essential in permitting the effective oral delivery of such molecules. Other publications and patent applications have disclosed other polysulfated disaccharides including, among many other compounds, the molecule shown as formula I herein. See, for example, WO2006017727A which discloses a compound of formula (1):

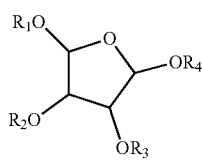

wherein R1, R2, R3 and R4 are independently selected from H, $C_{1-4}$alkyl, —SO3H, sulfated or unsulfated glycosyl or sulfated or unsulfated diglycosyl group with the proviso that at least one of R1-R4 is sulfated or unsulfated glycosyl or sulfated or unsulfated diglycosyl or salts thereof. Specific examples are also shown and described therein but the processes described in this publication produce impure forms of the examples. In addition, the processes disclosed require multiple protecting groups at various steps and disclose processes that result in greater than 1.5 wt % salt impurities in the final products. The present inventors have discovered a novel process that produces substantially pure crystalline polysulfated salts and, in particular, a substantially pure form of 2,5-Anhydro-3-O-(α-L-idopyranosyl)-D-mannitol hepta-O-sulfate salts. There is a need for heptasulfated disaccharides produced in substantially pure form and which are useful in highly bioavailable formulations for the treatment of pulmonary and other inflammatory disorders.

There is no disclosure in WO2006017727A of the improved oral bioavailability or higher potency of any of the compounds or examples therein nor is there any disclosure of the substantially pure forms of the drugs or of the particular dosage strengths recited and claimed herein for the treatment of asthma or any other indication. There is no teaching of oral dosage forms and strengths having improved LAR and EAR in in vivo sheep models. Surprisingly and unexpectedly, the present inventors have found that replacing the carboxylic acid moiety on the compounds disclosed in the '898 and '351 patents with a sulfate group on such polysulfated compounds along with producing a substantially pure form leads to compounds having remarkable oral bioavailability. There is thus no need to improve the bioavailability of such compounds with polymeric additives.

There is a need for an improved pulmonary or anti-inflammatory medication that is both efficacious and can be delivered in dosages to patients in need of treatment thereof on a convenient basis and which does not have the side effects associated with, for example, chronic administration of steroids or leukotriene receptor antagonists such as montelukast sodium. There is also a need to treat such diseases or conditions with a molecule having improved oral bioavailability in a suitable oral dosage form. In addition, there is a need for effective drugs that can be administered directly to the lungs in aerosol form that include the recited heptasulfated disaccharides along with optional and additional active pharmaceutical ingredients.

SUMMARY OF THE INVENTION

The present invention relates to pharmaceutical dosage forms comprising a substantially pure compound of formula I and pharmaceutically acceptable salts thereof and a pharmaceutical acceptable excipient. The preferred embodiment is salt of formula I wherein $R_1$-$R_7$ are SO3-Na+ The compounds in the dosage form are a compound of formula I or a pharmaceutically acceptable salt thereof,

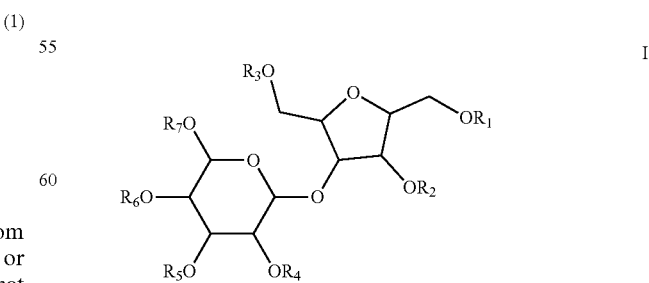

wherein $R_1$, $R_2$, $R_3$, $R_4$, $R_5$, $R_6$ and $R_7$ are selected from the group consisting of $SO_3H$ and pharmaceutically acceptable salts thereof. The present invention also relates to dosage forms having a substantially pure form of a compound of formula I. The invention further includes pro-drugs, derivatives, active metabolites, partially ionized and fully ionized derivatives of the compounds of formula I and stereoisomers thereof. The monomers which make up the disaccharides of the invention may be D or L isomers and the hydroxyl moieties or sulfated versions thereof around the carbocyclic ring (or acyclic versions or intermediates thereof) may have the alpha or beta designation at any particular stereocenter. The linking oxygen atom between the monosaccharide moieties may also be alpha or beta. The molecular weight of the compounds of the invention is typically less than 2,000 daltons. The preferred compound is 2,5-Anhydro-3-O-(a-L-idopyranase)-D-mannitol hepta-O-sulfate heptasodium salt.

The present invention also relates to a pharmaceutical dosage form comprising (i) a compound of formula I and pharmaceutically acceptable salts thereof wherein $R_1$, $R_2$, $R_3$, $R_4$, $R_5$ and R6 and $R_7$ are independently selected from $SO_3H$ or $PO_4H$ or salts thereof and (ii) a pharmaceutically acceptable excipient.

The present invention also encompasses a method of treating an inflammatory condition in an organism in need of treatment thereof comprising administering a pharmaceutically effective amount of a formulation comprising a compound of formula I

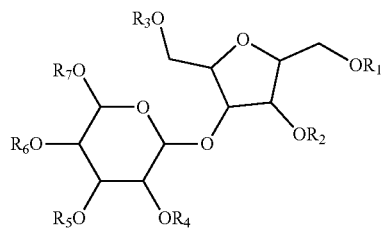

I and pharmaceutically acceptable salts thereof wherein $R_1$-$R_7$ are independently selected from $SO_3H$ or $PO_4H$.

The present invention also comprises a process for making a substantially pure form of a compound of formula I comprising the steps of preparing a compound of formula I wherein $R_{1-7}$ are H and sulfating said compound of formula I with a sulfating reagent to form the compound of formula I wherein $R_{1-7}$ are $SO_3H$ or a salt thereof. In a preferred embodiment, the process comprises combining intermediate 1a with intermediate 1b to form a compound of formula I wherein $R_{1-7}$ is selected from H.

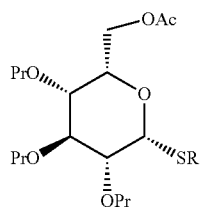

1a

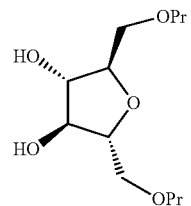

1b

In a more preferred embodiment, the present invention comprises a process for producing an intermediate compound of formula 1c, and protected versions thereof, from intermediates 1a and 1b and which is used to produce a compound of formula I herein in substantially pure form. In compound 1a, R is selected from a phenyl or tolyl moiety. Pr is a protecting group and may be selected from, for example, benzoyl or pivaloyl or other suitable protecting group. Thiophenyl or thiocresol are used as the thiolating reagents. Other thiolating reagents may also be used.

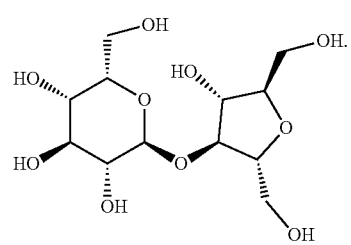

1c

The invention further comprises producing a substantially pure form of a compound of formula I from compound 1c comprising the steps of sulfating the compound of formula 1c and then purifying the heptasulfated disaccharide salt by running it through a Sephadex column; evaporating the solvent followed by trituration in ethanol. Other similar columns and solvents may be used provided the salt is obtained in substantially pure form.

BRIEF DESCRIPTION OF THE DRAWINGS

Aspects of the invention will be described in the following drawings.

in liquid form. $PD_{400}$ is defined as the provocating dose of carbochol in breath units which caused a 400% increase in $R_L$. One breath unit is one breath of 1% solution of carbochol. $PD_{400}$ is an indicator of airway responsiveness. The 0.5 mg/kg oral dose (QD for 4 days) inhibited EAR by 77%, LAR by 95% and AHR by 100%.

Figure 1A:
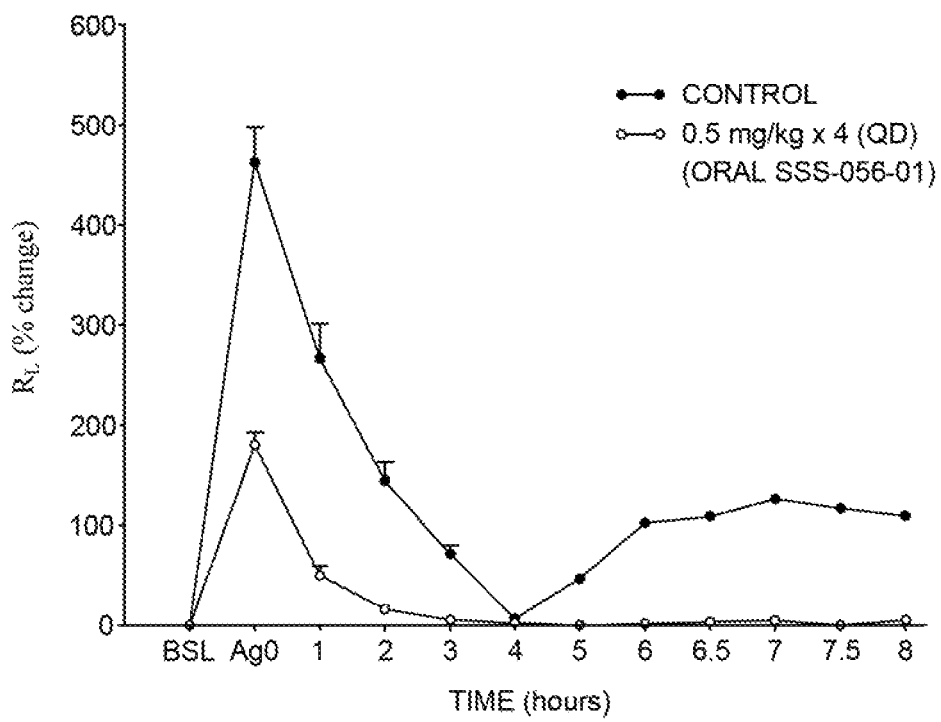
FIG. 1A shows a graph comparing the percentage change in pulmonary airflow resistance (measured as cm $H_2O$/L/sec) (i.e., the $R_L$) following the indicated time after antigen administration (time=0) of sheep's responses (n=5) to exposure to antigen only (closed circles) (control) and antigen plus a liquid oral dosage of 0.5 mg/kg×4 days (QD) of the heptasulfated disaccharide (sodium salt) designated as SSS-056-01*. The last dose was administered ninety minutes before antigen challenge (i.e., −1.5 hr). Data are shown as antigen-induced mean plus or minus SE % change in $R_L$ in sheep (n=5) exposed to antigen first with no drug and then again several weeks later with antigen plus SSS-056-01.
Figure 2A:
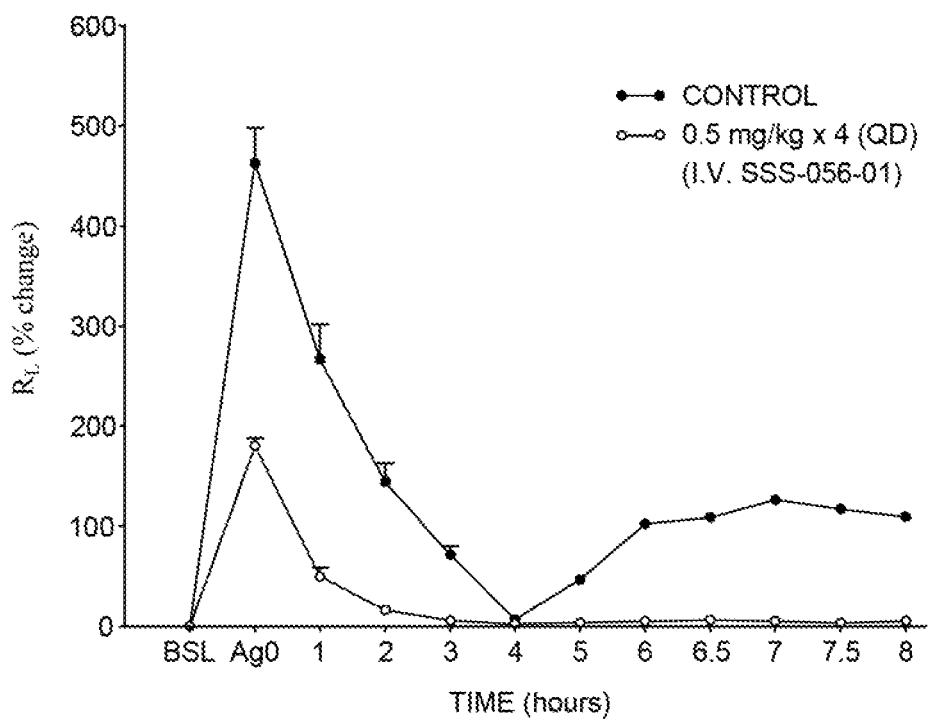

FIG. 2A shows a graph comparing the percentage change in pulmonary airflow resistance (i.e., the $R_L$) following the indicated time after antigen administration (time=0) of sheep's responses (n=5) to exposure to antigen only (closed circles) (control) and antigen plus an iv dose (0.5 mgs/kg×4 days (QD)) of the heptasulfated disaccharide designated as SSS-056-01 (open circles). The last dose was administered 90 minutes before antigen challenge (i.e., 1.5 hours). Data are shown as antigen-induced mean plus or minus SE % change in $R_L$ in sheep (n=5) exposed to antigen first with no drug and then again several weeks later with antigen plus SSS-056-01. The results show that there is no difference in bioavailability between the intravenous administered dose and the oral dose shown in FIG. 1A administered once a day.

Figure 1B:
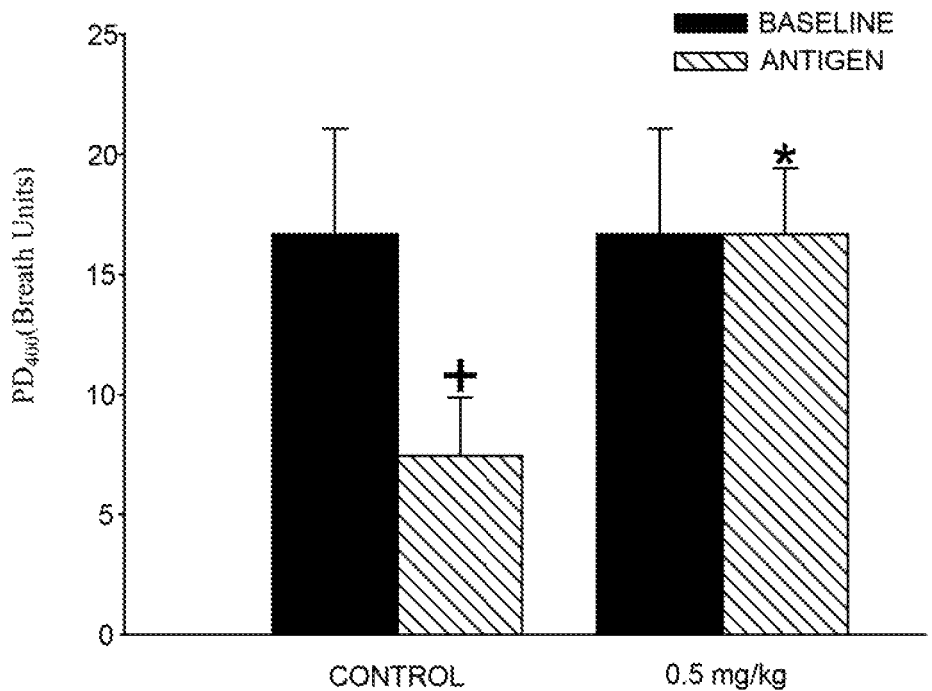
FIG. 1B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment (90 minutes beforehand) with an oral dose of SSS-056-01 (0.5 mg/kg×4 days (QD))
Figure 2B:
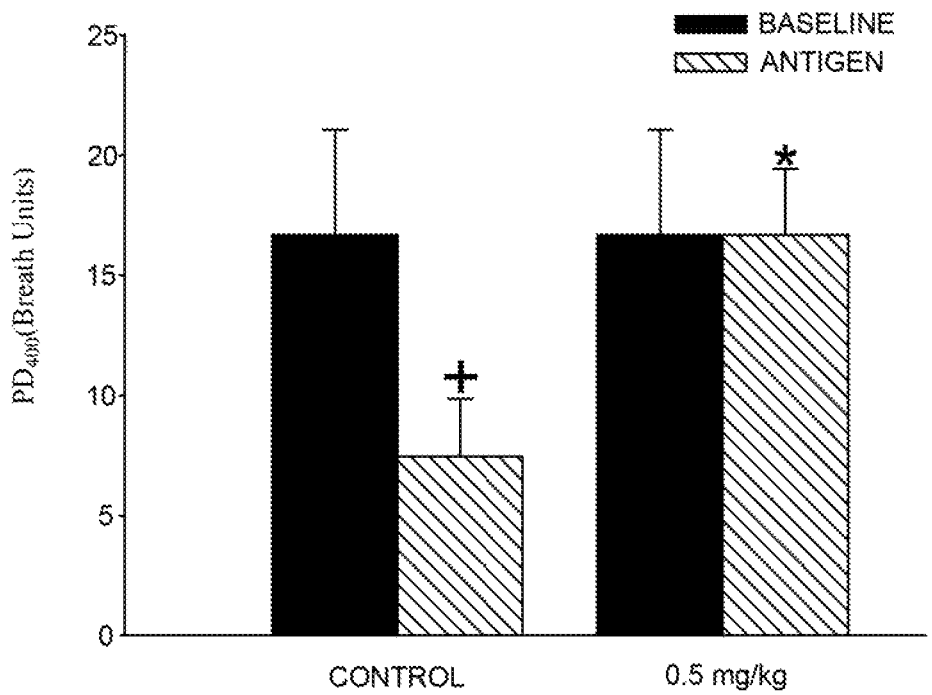

FIG. 2B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment (1.5 hours) with an iv. Dose (0.5 mgs/kg×4 days (QD)) of SSS-056-01. The results again show that there is no difference between the iv route of administration (bioavailability) and the oral route shown in FIG. 1B. The 0.5 mg i.v. dose (QD for 4 days) inhibited EAR by 77%, LAR by 92% and AHR by 100%.

Figure 3A:
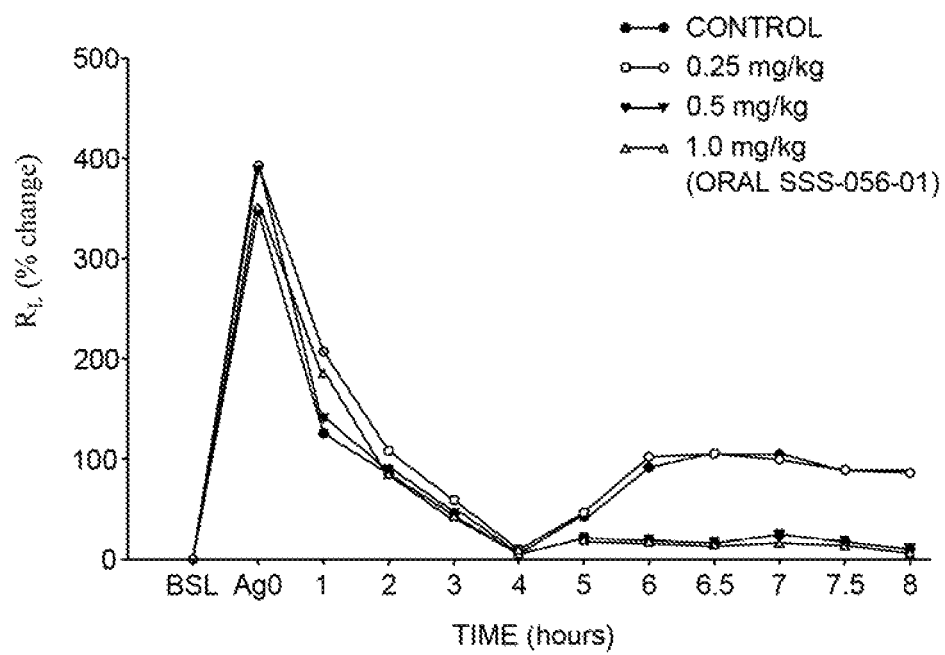

FIG. 3A shows a dose-response graph comparing the percentage change in pulmonary airflow resistance (measured as cm $H_2O/L/sec$) (i.e., the $R_L$) following the indicated time after antigen administration (time=0) of sheep's responses (n=5) to exposure to antigen only (closed circles) (control) and antigen plus a liquid oral dosage at various strengths (0.25 mg/kg (open circles); 0.5 mg/kg (closed triangles) and 1 mg/kg, (open triangles)) of the heptasulfated disaccharide designated SSS-056-01 (open circles). Data are shown as antigen-induced mean plus or minus SE % change in $R_L$ in sheep (n=5) exposed to antigen first with no drug and then again several weeks later with antigen after being pretreated with various oral doses of SSS-056-01 administered 90 min before antigen challenge.

Figure 3B:
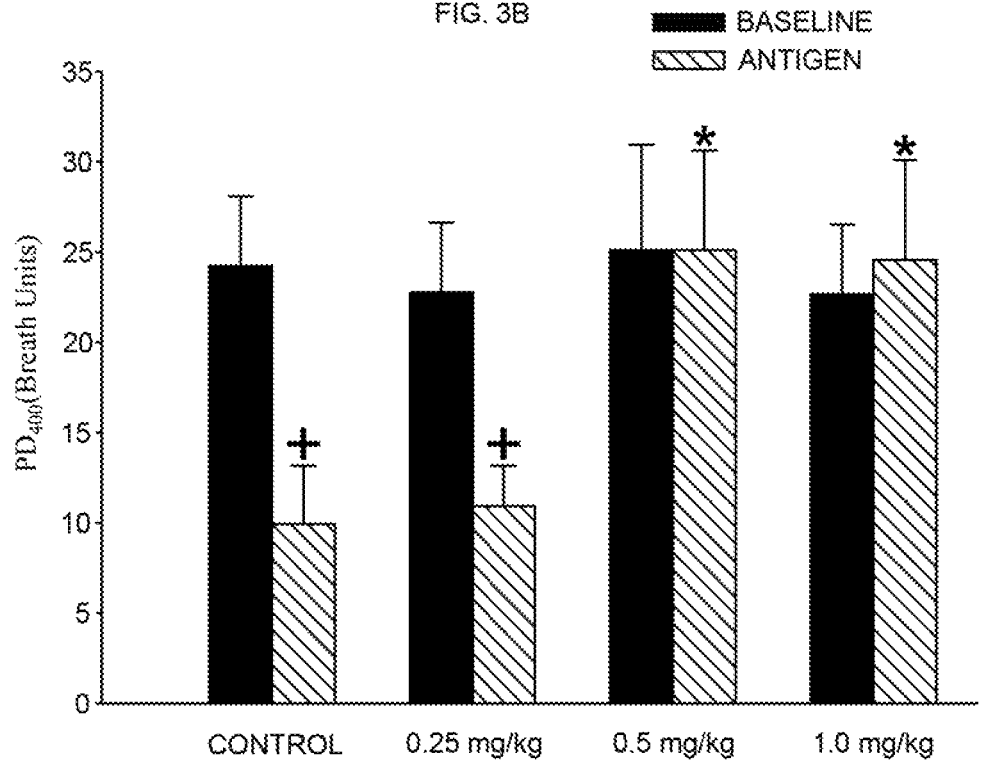

FIG. 3B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pre-treatment with various oral doses of SSS-056-01 (0.25 mgs/kg, 0.5 mgs/kg and 1.0 mgs/kg) administered 90 min. before the antigen challenge. +P<0.05 vs. baseline; and *P<0.05 vs. antigen control. The data in FIGS. 3A and 3B demonstrate that a single oral dose of SSS-056-01 at 0.25 mg/kg was ineffective while 0.5 mg/kg and 1 mg/kg inhibited LAR (71% and 77% inhibition) and AHR (100% inhibition) without an effect on EAR.

FIG. 4A shows a graph comparing the percentage change in pulmonary airflow resistance (measured as cm $H_2O/L/sec$) (i.e., the $R_L$) following the indicated time after antigen administration (time=0) of sheep's responses (n=5) to exposure to antigen only (closed circles, control) and antigen plus multiple (3× total; 1× every 12 hours) liquid oral doses of 0.25 mg/kg, 0.5 mg/kg and 1.0 mg/kg of the heptasulfated disaccharide designated as SSS-056-01, three weeks apart (open circles, solid triangle and open triangle respectively). Data are shown as antigen-induced mean plus or minus SE % change in $R_L$ in sheep (n=8) exposed to antigen first with no drug and then again several weeks later with antigen after being pretreated before antigen exposure with three doses each of 0.25 mg/kg, 0.5 mg/kg and 1.0 mg/kg SSS-056-01 (1× each 12 hr period, 3 weeks apart). Antigen challenge was ninety minutes after the last dose.

FIG. 4B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=8) exposed to antigen first with no drug and then again with antigen several weeks later following pre-treatment before exposure with a liquid oral dose of SSS-056-01 (0.25 mg/kg, 0.5 mg/kg and 1.0 mgs/kg) administered 1×3 each 12 hours. Antigen challenge was ninety minutes after the last mg/kg dose. The results show that the effect of multi-dose oral SSS-056-01 is cumulative. While 0.25 mg/kg×3 doses is ineffective; 0.5 mgs/kg×3 and 1 mg/kg×3 inhibited EAR (30% and 54% inhibition), LAR (85% and 87% inhibition) and AHR (100% inhibition). 1 mg/kg caused significantly greater inhibition of EAR than 0.5 mg/kg while the effect on LAR and AHR were comparable.

Figure 5A:
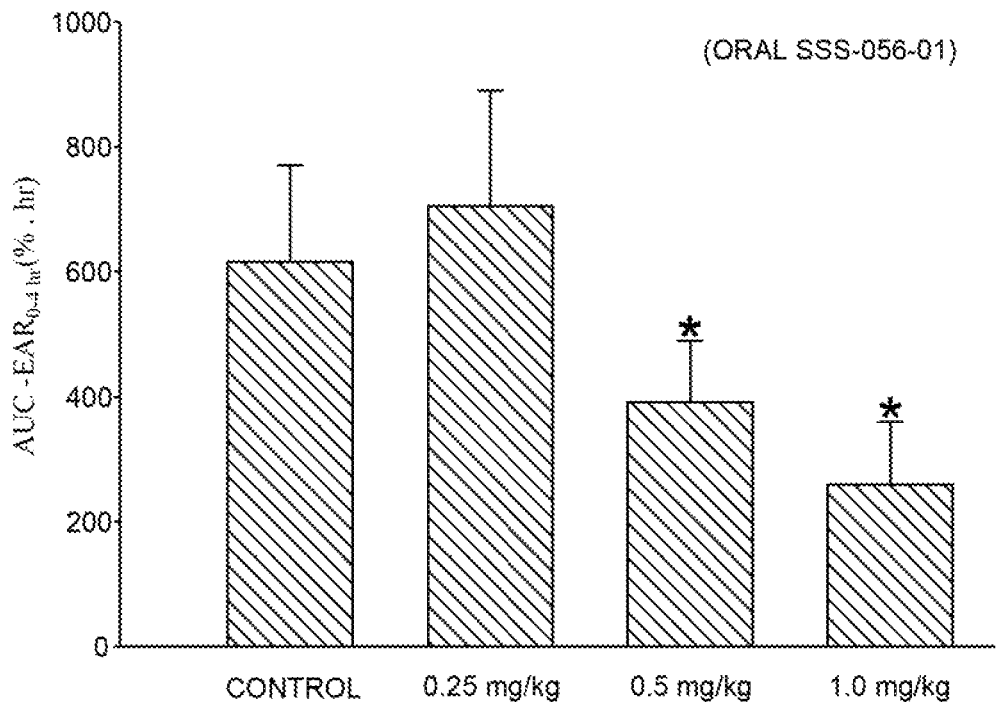

FIG. 5A shows the area under the curve for early phase (AUC-EAR$_{0-4}$ hr) from the data obtained in FIG. 4A.

Figure 5B:
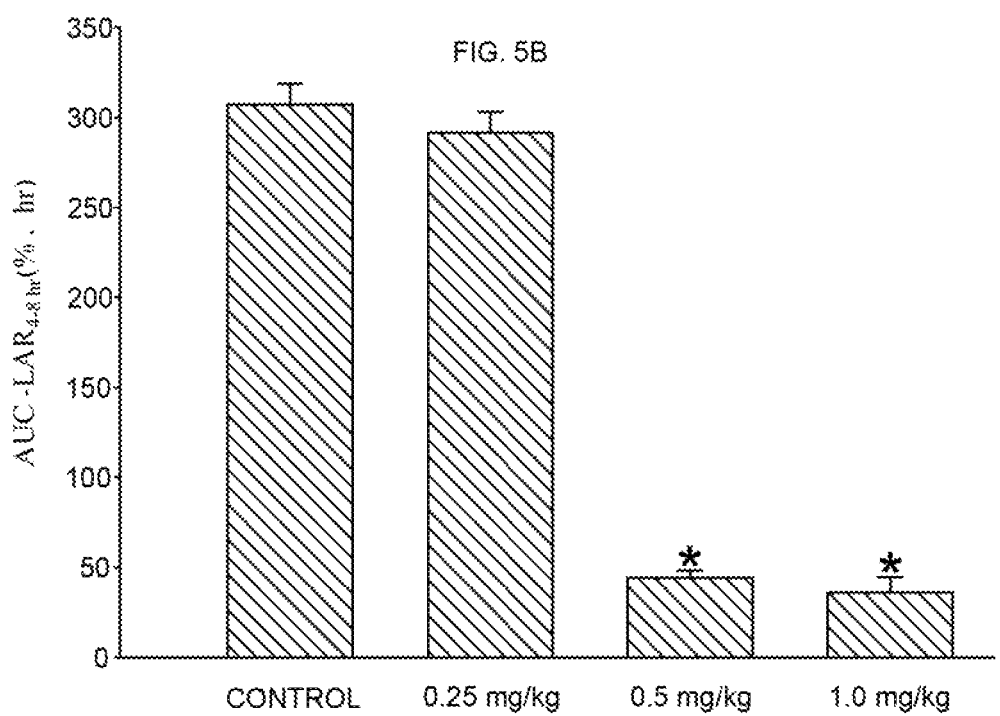

FIG. 5B shows the area under the curve for the late phase (AUC-LAR$_{4-8}$ hr) from the data obtain in FIG. 4A.

Figure 6A:
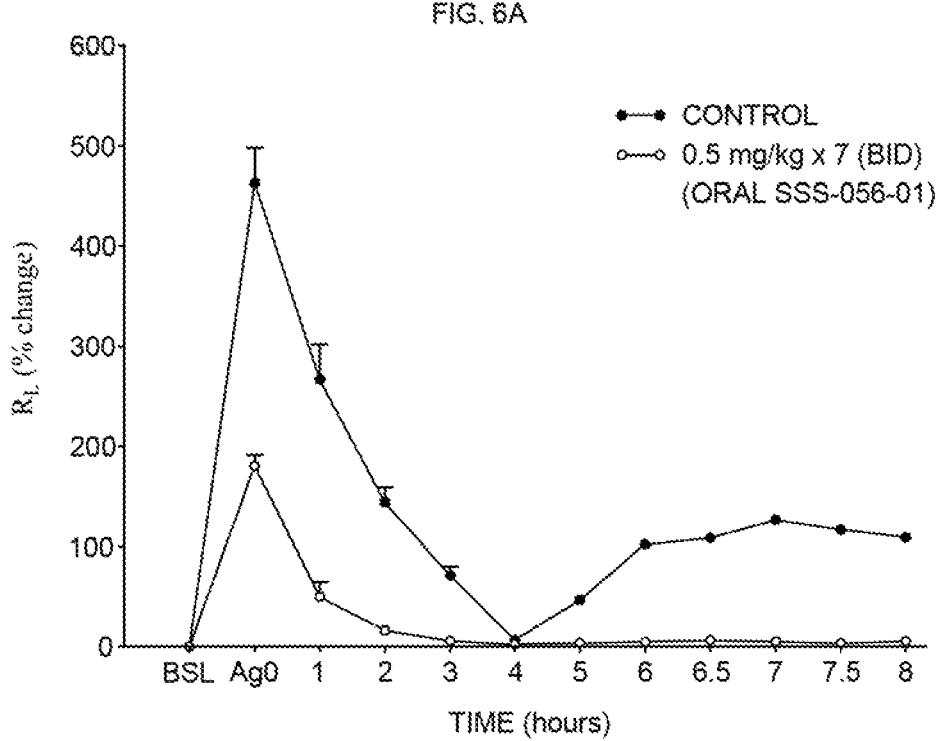

FIG. 6A shows a graph comparing the percentage change in pulmonary airflow resistance (measured as cm $H_2O/L/sec$) (i.e., the $R_L$) following the indicated time after antigen administration (time=0) of sheep's responses (n=5) to exposure to antigen only (closed circles) (control) and antigen plus a liquid oral dosage of 0.5 mg/kg administered twice a day (BID) for a total of seven doses of the heptasulfated disaccharide designated as SSS-056-01 (open circles). Data shown are antigen-induced mean plus or minus SE % change in $SR_L$ in sheep (n=5) exposed to antigen first with no drug and then again several weeks later with antigen after being pretreated before antigen exposure with the seven doses, the last dose was administered 90 minutes before the antigen challenge.

Figure 6B:
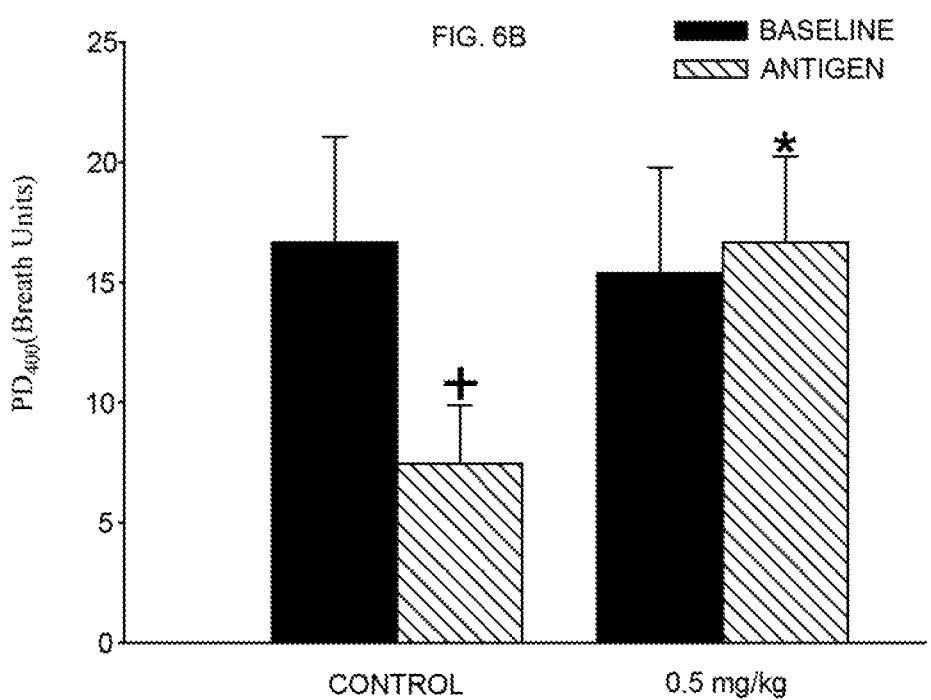

FIG. 6B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment with seven total doses administered every 12 hours before exposure with an oral dose of SSS-056-01 (0.5 mg/kg). Antigen exposure occurred ninety minutes after the last 0.5 mg/kg treatment. The data in FIGS. 6A and 6B show that the effect of multidose BID dosing of oral SSS-056-01 is cumulative. 0.5 mg/kg oral doses (BID×7 doses) inhibited EAR by 76%, LAR by 96% and AHR by 100%. This is significantly better than 0.5 mg/kg×3 doses. BID dosing (×7) is comparable to QD dosing (×4).

FIG. 7A shows the effect of multi-dose oral SSS-056 on antigen-induced EAR, LAR and AHR in sheep (QD dosing). Oral SSS-056-01 (0.5 mg/kg) was administered once daily in the morning×4 days, and antigen challenge was performed 90 minutes after the last dose (n=5). EAR and LAR are shown as antigen-induced % change in $R_L$±SE, without (control, closed circles) and after treatment with oral SSS- 056-01 (open circles). The results also show that the effect of multi-dose oral SSS-056-01, BID versus QD dosing is comparable.

FIG. 7B shows post-antigen AHR shown as mean±SE $PD_{400}$ for the baseline and 24 hours post-antigen without (control) and after treatment with SSS-056-01. +P<0.05 vs. Baseline; *P<0.05 vs. antigen control.

*This compound is also described herein as SSS-02.

Figure 8A:
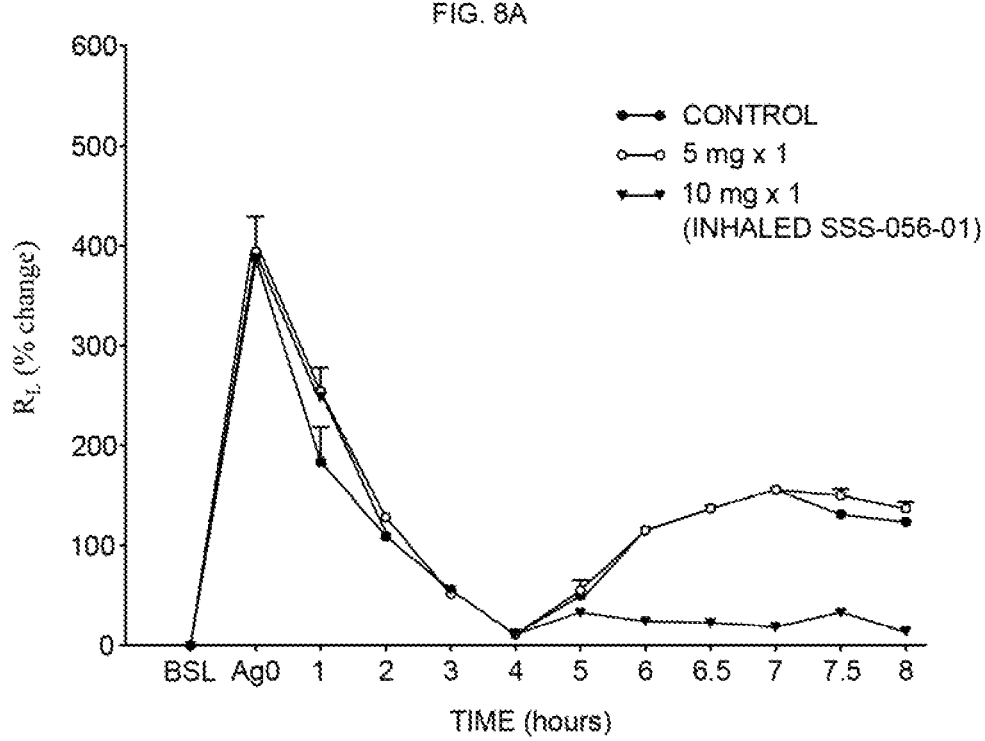

FIG. 8A shows the effect of single dose "inhaled" SSS-056 on antigen-induced EAR, LAR and AHR in sheep (n=5). Inhaled SSS-056-01 in bacteriostatic injection water was administered 30 minutes before antigen challenge. EAR and LAR are shown as antigen-induced % change in $R_L$±SE without (control) and after treatment with various doses of SSS-056-01.

Figure 8B:
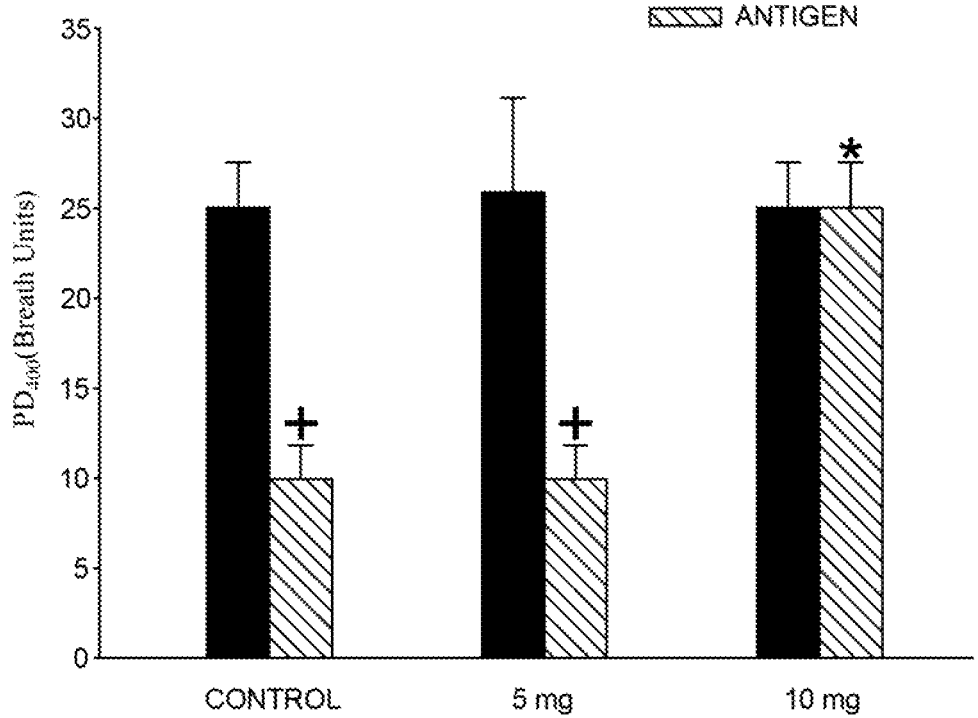

FIG. 8B shows post antigen AHR shown as mean+/−SE PD400 for the baseline and 24 hour post-antigen, with (control) and after treatment with 5 mg and 10 mg inhaled SSS-056-01. This shows that 10 mg single dose of inhaled SSS-056-01 inhibits LAR (75% inhibition) and AHR (100% inhibition) without an effect on EAR; while the 5 mg dose was ineffective.

Figure 9A:
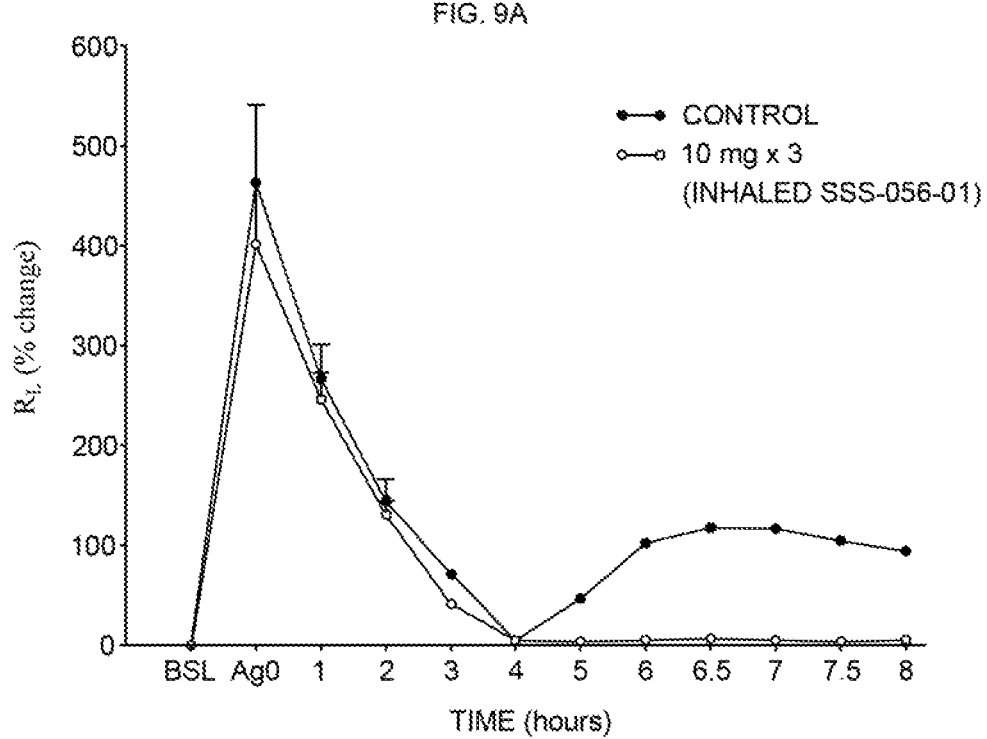

FIG. 9A shows multi-dose inhaled SSS-056-01 (10 mg×3) had no significant cumulative effect on EAR (n=6), but did inhibit LAR. The data was comparable to a single dose, as shown in FIG. 8.

Figure 9B:
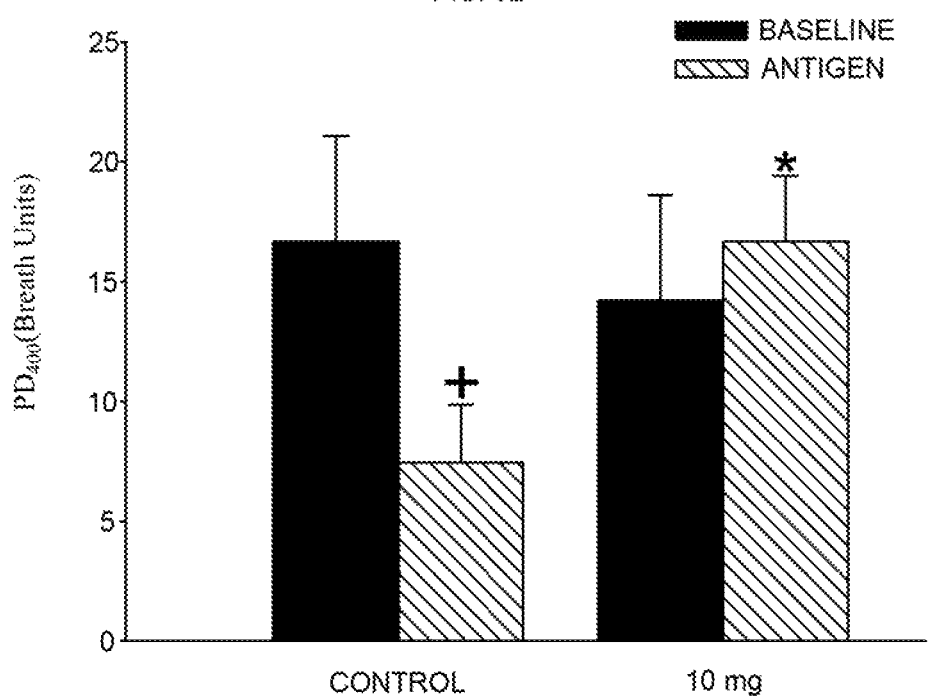

FIG. 9B shows post antigen AHR shown as mean SE PD400 for the baseline and 24 hour post-antigen, with (control) and after treatment with 10 mg×3 inhaled SSS-056-01. This shows that multiple dose (10 mg×3) of inhaled SSS-056-01 inhibits LAR (75% inhibition) and AHR (100% inhibition) without an effect on EAR.

Figure 10:
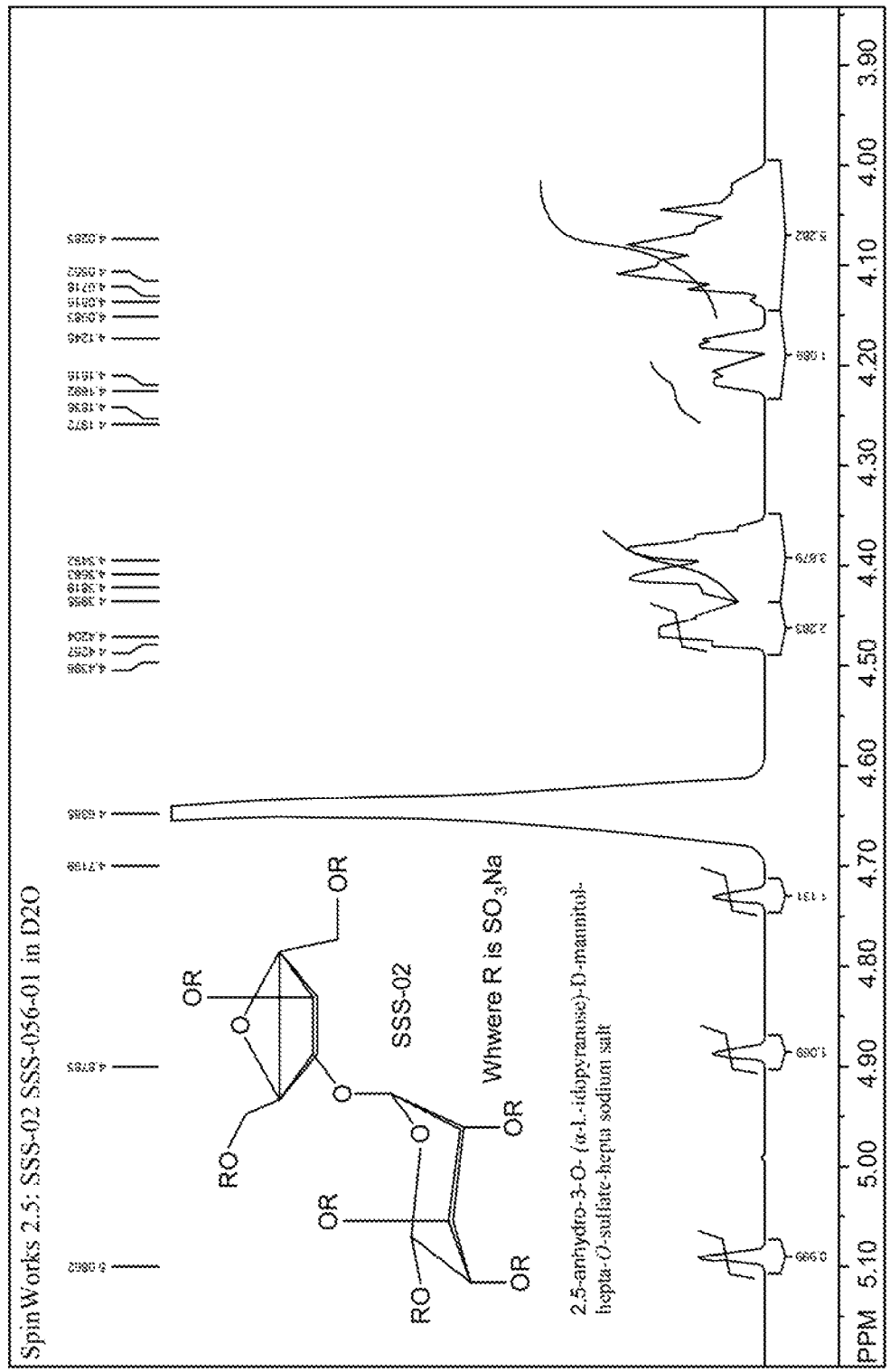

FIG. 10 shows the proton NMR of SSS-056-01 (2,5-anhydro-3-O-(α-L-idopyranose)-D-mannitol-hepta-O-sulfate-hepta sodium salt).

DETAILED DESCRIPTION

The present invention comprises a substantially pure form of a compound of formula I:

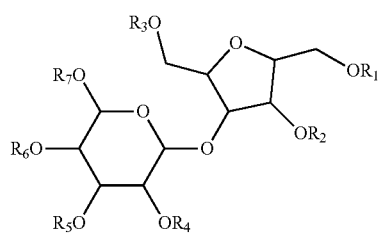

I wherein $R_1$, $R_2$, $R_3$, $R_4$, $R_5$ and $R_6$ and $R_7$ are independently selected from the group consisting of $SO_3H$ or $PO_3H$ or pharmaceutically acceptable salts thereof.

The present invention relates to pharmaceutical formulations and uses thereof wherein the formulation comprises a substantially pure compound of formula I and pharmaceutically acceptable salts thereof

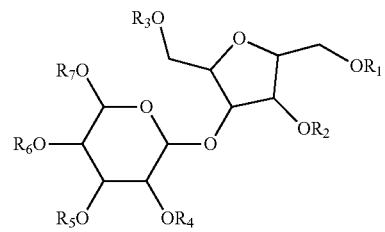

I wherein $R_1$, $R_2$, $R_3$, $R_4$, $R_5$ and $R_6$ and $R_7$ are independently selected from the group consisting of $SO_3H$ or $PO_3H$.

The present invention also relates to a pharmaceutical formulation comprising (i) a substantially pure form of a compound of formula I and pharmaceutically acceptable salts thereof

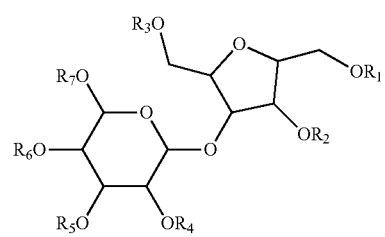

I wherein $R_1$-$R_7$ are selected from $SO_3H$ or pharmaceutically acceptable salts thereof and (ii) a pharmaceutically acceptable excipient.

The present invention also relates to oral dosage forms comprising a compound of formula I and their pharmaceutically acceptable salts with $R_1$-$R_7$ as defined above.

The present invention further comprises a formulation comprising a product produced by a process of reacting compound 1a with compound 1b to form compound 1c and which is sulfated to form a substantially pure heptasulfated salt form of such compound and a pharmaceutically acceptable excipient.

The present invention also encompasses a method of treating or alleviating an inflammatory condition comprising administration of an oral dosage form of (i) a pharmaceutically effective amount of a formulation comprising a substantially pure compound of formula I

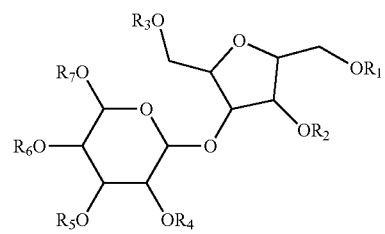

I and pharmaceutically acceptable salts thereof wherein $R_1$-$R_7$ are independently selected from $SO_3H$, $PO_3H$ wherein the oral dosage form has comparable bioavailability to an intravenous administered dosage form.

The present invention further relates to a method of treating an inflammatory condition comprising administering an oral dosage form of between 0.25 to 10.0 mgs/kg/day to a patient in need of treatment thereof.

The present invention also comprises i.v. formulations of the substantially purified form of a compound of formula I as well as inhalable formulations.

In a preferred embodiment, the compounds in the formulation are selected from a metal salt of a compound of formula I wherein each sulfate or phosphate group around the disaccharide is ionized to form a metal salt wherein the metals are selected from, for example, sodium or potassium. In addition, other salts including amine salts may form at such positions. The most preferred compound is compound 1c in the fully sulfated and ionized form as the sodium salt.

It is generally understood that the source of the polysaccharide which generates the disaccharides utilized in the formulations of the invention will determine, for the most part, the absolute stereochemistry of the chiral centers around the carbohydrate rings. Additional sulfate groups are added by chemical means by the process described generally above or by any known means to afford the most active moieties (hypersulfated disaccharides and salts thereof) which are further purified to form pharmaceutical grade disaccharides which are further formulated with an optional additive and processed into a dosage form suitable for administration to a mammal or other organism in need of treatment thereof.

Nuclear magnetic resonance imaging and/or other known structure identification methods may be used to determine the chemical structures of the molecules described herein (see FIG. 10).

A compound of formula I in the described strengths is formulated with a pharmaceutically acceptable excipient to form the formulations of the invention.

The formulations of the invention can be delivered to the patient or other organism by any suitable known means. The percentages of the additive and type of additive added to the formulation relative to the active ingredient and other excipients will be based upon the type of formulation desired. For example, in an oral suspension formulation to be delivered to a patient or organism in need of treatment thereof, the vehicle can be an oral liquid or oral capsule. The preferred formulation is an oral capsule.

The compositions of the invention further comprise pharmaceutically acceptable excipients and/or fillers and extenders such as lactose or other sugars including but not limited to glucose, sucrose, mannitol etc. and lubricants such as magnesium stearate, talc, calcium stearate, solid polyethylene glycols, sodium lauryl sulfate and mixtures thereof. The amount of filler or lubricant or other known pharmaceutically acceptable additive will vary based upon the type of formulation and the manner the formulation is processed or made.

The compositions of the invention can be delivered or administered orally in the form of tablets, capsules or suspensions. The tablets or capsules can be prepared by means known in the art and contain a therapeutically effective amount of a hypersulfated disaccharide of formula I with $R_{1-7}$ as defined herein. Tablets and pills or other suitable formulations can be prepared with enteric coatings and other release controlling coatings. Coatings can be added to afford light protection or swallowability. The capsules and tablets or suspensions can include additives which improve the taste of the medicine.

Liquid dosage forms for oral administration may include pharmaceutically acceptable emulsions, solutions, suspensions, syrups and elixers containing inert diluents such as water as well as the compounds of formula I and salts thereof. Such formulations may additionally include adjuvants including wetting agents, emulsifying and suspending agents, and sweetening, flavoring and perfuming agents. The compounds of the invention may be formulated in a sustained release or delayed release formulation. The compounds may thus be formulated into extended release dosage forms comprising a compound of formula I or a pharmaceutically acceptable salt thereof. Such formulations can include matrix formulations having extended release components such as cellulosic polymers.

The compounds of formula I form, as stated above, pharmaceutically acceptable salts. The metal salts include for example salts having Na, K, Ca, Ng or Ba or Al, Zn, Cu, Zr, Ti, Bi, Mn or Os or salts formed by reacting the compounds of formula I with an organic base such as an amino acid or with any amine. The preferred salt is a sodium salt.

These formulations are useful in treating a number of inflammatory diseases and conditions. Types of respiratory diseases or conditions contemplated herein include allergic rhinitis which is characterized by seasonal or perennial sneezing, rhinorrhea, nasal congestion, and often conjunctivitis and pharyngitis; acute rhinitis, characterized by oedema of the nasal mucosa, nasal discharge and mucosa. Pulmonary diseases, such as intrinsic or extrinsic asthma bronchiale, any inflammatory lung disease, acute chronic bronchitis, pulmonary inflammatory reactions secondary to chronic bronchitis, chronic obstructive lung disease, cystic fibrosis, pulmonary fibrosis, ARDS, acute lung injury, Goodpasture's syndrome as well as any lung disease or condition in which white blood cells may play a role including idiopathic pulmonary fibrosis and any other autoimmune lung disorders are treatable with the formulation of the invention.

Ear, nose and throat disorders such as acute external otitis, furunculosis and otomycosis of the external ear are treatable by the formulations of the invention. Other conditions include respiratory diseases such as traumatic and infectious myringitis, acute Eustachian salpingitis, acute serous otitis media and acute and chronic sinusitis.

Formulations of the invention are useful in treating pulmonary inflammation. The term "pulmonary inflammation" encompasses any inflammatory lung disease, acute chronic bronchitis, chronic obstructive lung disease, pulmonary fibrosis, Goodpasture's syndrome, and any pulmonary condition in which white blood cells may play a role including but not limited to idiopathic pulmonary fibrosis and any other autoimmune lung disease.

Formulations of the invention are useful in treating asthma and asthma related pathologies. The term "asthma" means a condition of allergic origin, the symptoms of which include continuous or paroxysmal labored breathing accompanied by wheezing, a sense of constriction in the chest, and, often, coughing or gasping. The term "asthma related pathologies" means a condition whose symptoms are predominantly inflammatory in nature with associated bronchospasm. Both asthma and an asthma related pathology are characterized by symptoms which include a narrowing of the airways, varying over short periods of time either spontaneously or as a result of a treatment, due in varying degrees to contraction (spasm) of smooth muscle, edema of the mucosa, and mucus in the lumen of the bronchi and bronchioles. Generally these symptoms are triggered by local release of spasmogens and vasoconstrictive substances (e.g. histamine or certain leukotrienes or prostaglandins) in the course of an allergic response. Non-limiting examples of asthma related pathologies include non-asthmatic conditions characterized by airway hyperresponsiveness (e.g. chronic bronchitis, emphysema and cystic fibrosis). The most prominent characteristic of asthma is bronchospasm, or narrowing of the airways: asthmatic patients have prominent contraction of smooth muscles of large and small airways, increased mucous production, and increased inflammation. The inflammatory response in asthma is typical for tissues covered by mucosa and is characterized by vasodilation, plasma exudation, recruitment of inflammatory cells such as neutrophils, monocytes, macrophages, lymphocytes, and eosinophils to the sites of inflammation and the release of inflammatory mediators by resident tissue cells (mast cells) or by migrating inflammatory cells (J. C. Hogg, "Pathology of Asthma," Asthma and Inflammatory Disease, P. O'Byren (ed.), Marcel Dekker, Inc., New York, N.Y. 1990, pp. 1-13).

Asthma may be triggered by multiple or a variety of causes such as in response to allergens, secondary exposure to infective agents, industrial or occupational exposures, ingestion of chemicals, exercise and/or vasculitis (Hargreave et al., J. Allergy Clinical Immunol. 83:1013-1026, 1986). As discussed herein, there may be two phases to an allergic asthma attack—an early phase and a late phase which follows 4-6 hours after bronchial stimulation (Harrison's Principles of Internal Medicine $14^{th}$ Edl, Fauci et al. (eds), McGraw Hill, New York, N.Y. 1998, pp. 1419-1426). The early phase which typically resolves spontaneously, includes the immediate inflammatory response including the response caused by the release of cellular mediators from mast cells. The late phase reactions develop over a period of hours and are characterized histologically by an early influx of polymorphonuclear leukocytes and fibrin deposits followed by infiltration of eosinophils. A certain percentage of patients are "dual responders" and develop an early acute and a late phase response. In dual responders, the acute phase is followed 4-14 hours later by a secondary increase in airway resistance ("late phase response" or LPR or "late airway response" or LAR). Late responders and dual responders are of particular clinical importance because, in combination with the airway inflammation, late phase responses lead to a prolonged airway hyperreactivity (AHR), asthmatic exacerbations, or hyperresponsiveness, worsening of symptoms, and generally a more severe form of clinical asthma that may last from days to months in some subjects, requiring aggressive therapy. Pharmacological studies in allergic animals have demonstrated that not only the bronchoconstrictor response but also the inflammatory cell influx and the mediator release pattern in dual responders is quite different from acute responders.

An increase in bronchial hyperreactivity (AHR), the hallmark of a more severe form of asthma, can be induced by both antigenic and non-antigenic stimuli. Late phase response, allergen-induced asthma and persistent hyperresponsiveness have been associated with the recruitment of leukocytes, and particularly, eosinophils, to inflamed lung tissue (W. M. Abraham et al., Am. Rev. Respir. Dis. 138: 1565-1567, 1988). Eosinophils release several inflammatory mediators including 15-HETE, leukotriene C4, PAF, cationic proteins and eosinophil peroxidase.

Moreover, the formulations of the invention are also useful in treating late phase reactions and inflammatory response in extra pulmonary sites such as allergic dermatitis, inflammatory bowel disease; rheumatoid arthritis and other collagen vascular diseases, glomerulonephritis, inflammatory skin diseases and conditions; and sarcoidosis.

As used herein, the term "treating or alleviating the symptoms" means reducing, preventing and/or reversing the symptoms of the individual to which a formulation of the invention has been administered as compared to the symptoms of the individual or an individual which is untreated. Hence, a formulation of the invention that treats or alleviates the symptoms of asthma or an asthma related pathology reduces, prevents, and/or reverses the early phase asthmatic response to antigen challenge in a dual responder individual, more preferably reduces, prevents and/or reverses the late phase asthmatic response to antigen challenge in a dual responder individual, and more preferably reduces, prevents and/or reverses both the early phase and late phase responses to antigen challenge in a dual responder individual. This "treatment" or "alleviation" is preferably a significant percentage as shown in the animal models presented herein for the recited formulations and with respect to LAR and AHR data.

The terms "antigen" and "allergen" are used interchangeably to describe those substances such as dust or pollen that can induce an allergic reaction and/or induce an asthmatic episode or asthmatic symptoms in an individual suffering from such condition. Thus an individual is "challenged" when an allergen or antigen is present in a sufficient amount to trigger an asthmatic response in such individual. The term "substantially pure" means that the purified compound has less than 1.5 weight percentage of any impurity exclusive of solvents or moisture.

It is also understood that the formulations of the invention are useful in treating any disease or condition affected by late phase reactions (LPR's). The airways are merely a prototype of organs or tissues affected by such LPR's. It has been established in the medical literature that the last phase bronchoconstriction and AHR observed in dual responder asthmatic patients is not an isolated phenomenon restricted to asthmatic or even pulmonary patients. Thus, the present formulation is useful in treating any disease or condition affected by LPR's including cutaneous, nasal, ocular and systemic manifestations of LPR's in addition to pulmonary associated LPR's. Clinical diseases (whether of the skin, lung, nose, eye or other organs) recognized to involve allergic mechanisms have a histologic inflammatory component which follows the immediate allergic or hypersensitivity reaction that occurs on antigen challenge. This sequence of response appears to be connected to mast cell mediators and propagated by other resident cells within target organs or by cells recruited into the sites of mast cell or basophilic degranulation. Thus, the present formulation is useful in treating inflammatory bowel disease, rheumatoid arthritis, glomerulonephritis and inflammatory skin disease. The present invention therefore relates to a method of treating a patient or organism in need of treatment thereof and who/which is suffering from a disease or condition characterized by late phase allergic reactions, including e.g, and without limitation, pulmonary, nasal, cutaneous, ocular and systemic LPR's, and/or which is characterized by inflammatory reactions through the administration, by any known means, of a formulation comprising a compound of formula I or II and a delivery agent such as, for example, a polymeric additive to said patient or organism.

The term "inflammatory condition" means a disease, condition or symptom selected from the group consisting of pulmonary inflammation such as asthma and/or asthma related pathologies; pneumonia, tuberculosis, rheumatoid arthritis, allergic reactions which impact the pulmonary system, early and late phase responses in asthma and asthma related pathologies, diseases of the small and large airways of the lung, bronchospasm, inflammation, increased mucus production, conditions which involve vasodilation, plasma exudation, recruitment of inflammatory cells such as neutrophils, monocytes, macrophages, lymphocytes and eosinophils and/or release of inflammatory mediators by resident tissue cells (mast cells); conditions or symptoms which are caused by allergens, secondary responses to infections, industrial or occupational exposures, ingestion of certain chemicals or foods, drugs, exercise or vasculitis; conditions or symptoms which involve acute airway inflammation, prolonged airway hyperreactivity, increases in bronchial hyperreactivity, asthmatic exacerbations, hyperresponsiveness; conditions or symptoms which involve the release of inflammatory mediators such as 15-HETE, leukotriene C4, PAF, cationic proteins or eosinophil peroxidases; conditions or symptoms which relate to cutaneous, nasal, ocular or systemic manifestations of late phase allergic responses; clinical diseases of the skin, lung, nose, eye or throat or other organs and which involve allergic mechanisms having an histologic inflammatory component upon antigen challenge; allergic rhinitis, respiratory diseases characterized by seasonal or perennial sneezing; rhinorrhea, conjunctivitis, pharyngitis, intrinsic or extrinsic asthma bronchiale, any inflammatory lung disease, acute chronic bronchitis, pulmonary inflammatory reactions secondary to acute chronic bronchitis, chronic obstructive lung disease (COPD), pulmonary fibrosis, Goodpasture's syndrome, any pulmonary condition in which white blood cells play a role including but not limited to idiopathic pulmonary fibrosis and any other autoimmune lung disease; ear, nose and throat disorders such as acute external otitis, furunculosis and otomycosis of the external ear; respiratory diseases such as traumatic and infectious myringitis, acute eustachian salpingitis, acute serous otitis media, acute and chronic sinitis; extrapulmonary conditions selected from any late-phase reactions and inflammatory response such as allergic rhinitis; allergic dermatitis; allergic conjunctivitis; extrapulmonary diseases where inflammation occurs and/or an inflammatory response plays a major role including inflammatory bowel disease; rheumatoid arthritis and other collagen vascular diseases; glomerulonephritis; inflammatory skin diseases and sarcoidosis and cardiovascular inflammation as described below. The compounds may also be used to treat central nervous system disorders such as Alzheimer's disease, including the inhibition of β-amyloid aggregation in Alzheimer's disease and neuroinflammation.

The present substantially pure compounds and formulations thereof may also be utilized to treat inflammatory conditions associated with cardiovascular disease. It is known that there are serious side effects associated with traditional anti-inflammatory agents such as glucocorticoid steroids and cyclophosphamide making them inappropriate choices for atherosclerotic inflammation treatment. On the other hand, the polysulfated disaccharide formulations of the invention have the advantage of having few side effects along with anti-inflammatory properties. It has clearly been postulated that atherosclerotic lesions are due to or have many properties associated with chronic inflammation including the presence of macrophages, lymphocytes and denditric cells which accumulate at specific loci to cause and/or acerbate lesions. L. K. Curtiss, N. Engl. J. Med. 360; 11 1144-1146 (2009). The present formulation is thus useful for the treatment of arteriosclerotic disorders in patients having such disorders or conditions and is further useful in the treatment or prevention of restenosis after invasive vascular surgery or after an organ transplant. The formulation suitable for cardiovascular treatment can be administered by any known means including by interal or parenteral administration. The present invention comprises a method of treating cardiovascular inflammation comprising administration of a composition comprising a substantially pure compound of formula I wherein R1-R7 are as defined herein and pharmaceutically acceptable salts thereof and a pharmaceutically acceptable excipient to a patient in need of treatment thereof. The present invention further includes combinations of a compound of formula I with R1-R7 as defined herein and a cardiovascular drug selected from an HMGCoA reductase inhibitor or other cardiovascular drug or drugs used to treat cardiovascular disease. The "combination" may be in the form of a single dosage form having at least two active ingredients wherein one of the active ingredients is a hypersulfated disaccharide of the invention and the other active ingredient is selected from an HMGCoA reductase inhibitor such as lovastatin, simvastatin, atorvastatin or rosavastatin calcium. In a preferred embodiment, the combination would include a formulation of the invention comprising a compound of formula I or II wherein $R_1$-$R_7$ is as defined herein and a second active ingredient selected from an HMGCoA reductase inhibitor.

The formulations of the invention have been found to be effective in animal studies which are predictive of utility in humans as well as other animals. The animal studies demonstrate that the substantially pure compounds and formulations thereof are useful in (a) preventing antigen-induced bronchoconstrictor response and bronchial hyperactivity (also referred to as airway-hyperresponsiveness (AHR)) and (b) in ameliorating AHR subsequent to antigen challenge in treated animals. Pulmonary airflow resistance was measured by taking allergic sheep previously verified as dual bronchoconstrictor responders to *Ascaris suum* antigen. The sheep were intubated with a cuffed nasotracheal tube and pulmonary airflow resistance ($R_L$) was measured by the esophageal balloon catheter technique. Airway responsiveness was determined by first securing cumulative dose response curves to inhaled carbachol (a constrictor agonist) by measuring $R_L$ before and after inhalation of buffered saline and after each administration of 10 breaths of increasing concentrations of carbachol (0.25, 0.5, 1.0, 2.0 and 4.0% wt/vol solution). Airway responsiveness was measured by determining the cumulative provocation dose ($PD_{400}$) of carbachol (in breath units) that increased $R_L$ to 400% above baseline. One breath unit was defined as one breath of 1% carbachol solution.

As appropriate, and according to the prescribed method of administration, the substantially pure compounds of formula I as defined herein and formulations thereof may be administered prior to, at the same time, or after the organism or patient has been exposed to an antigen and in relation to the particular disease or condition being treated. Doses of the active ingredient (the hypersulfated disaccharides of formula I) preferably range from 1 mgs/kg to 5 mg/kg per day. These doses may be adjusted by the physician depending upon the response of the patient. Oral doses are preferred. Suitable dose ranges may include 0.05 mgs/kg/day to 25 mgs/kg/day.

The formulations of the invention may be administered alone or in combination with other suitable medications or active ingredients and depending upon the particular disease or condition being treated. In a preferred embodiment, the formulations or compounds of the invention are administered in the morning or evening. Thus, the present invention comprises a method of treating a disease or condition associated with antigen exposure and which involves an early and late phase response comprising administering to an organism in need thereof a therapeutically effective amount of a compound of formula I with $R_1$-$R_7$ as defined herein wherein the formulation is administered in the morning or evening. The invention further comprises a method of treating a disease or condition associated with antigen exposure and which involves an early and late phase response comprising administering to an organism in need thereof a therapeutically effective amount of a compound of formula I with $R_1$-$R_7$ as defined herein to form a formulation and wherein said formulation is administered to the organism in the morning or evening. The additional active ingredients that may be administered in the form of combination therapy or in the form of a single dosage unit having at least two active ingredients wherein the first active is a compound of formula I with $R_1$-$R_7$ as defined herein and a second active selected from any drug or medicament which is used as front line therapy to treat asthma or an asthma related disorder or condition or other inflammatory condition as recited herein. Such medicaments include anti-inflammatories, leukotriene antagonists or modifiers, anticholinergic drugs, mast cell stabilizers, corticosteroids, immunomodulators, beta-adrenergic agonists (short acting and long acting), methyl xanthines, and other general classes or specific drugs used to treat such disorders including, but not limited to, montelukast sodium; albuterol; levoalbuterol; salmeterol; vilanterol, indacaterol, formoterol, fluticasone propionate; budesonide; ceterizine; loratadine; desloratadine; theophylline, ipratropium, cromolyn, nedocromil, beclomethasone, flunisolide, mometasone, triaminoclone, prednisoline, prednisone, zafirlukast, zileuton or omalziunab and other disaccharides.

The substantially pure compounds of the invention have surprisingly high bioavailability relative to, for example, hexasulfate disaccharides or relative to impure forms of the drug. It is postulated that even the presence of minor salt impurities (e.g. 1.5-2%) renders the drug less bioavailable. The combination of both purity and the elimination of the carboxylic acid group on hexasulfated analogs also yields surprisingly high relative bioavailability. The present inventors have found that an oral dosage form of the substantially pure form of 2,5-anhydro-3-O-(α-L-idopyranosyl)-D-mannitol hepta-O-sulfate sodium salt has comparable bioavailability to the intravenous form. In addition, the inventors have found that the heptasaccharide is more potent on a mg/mg basis than the same dosage strength of the comparable hexadissacharide having a carboxylic acid moiety or salt thereof and, furthermore, does not require a polymeric additive to improve bioavailability.

The compounds of formula I were prepared by a process which synthesized two building blocks—an α-idopyranose and a D-mannitol. In general, as shown in the scheme below, the two building blocks are reacted with each other to form the disaccharide which is further processed to form the polysulfated salts. The present inventors have found deficiencies in the prior art processes that led to significant impurities in the final product. The inventors have solved the problems of creating a purer product by directly purifying the final product on a Sephadex column, followed by evaporation of the solvent and trituration with ethanol. This process avoids contamination by traces of sodium acetate which are in the final product produced by the process disclosed in WO20060177727 using other solvents such as methanol and different purification procedures. Surprisingly, the replacement of methanol with ethanol yielded significant and unpredictable improvements. In addition to this improvement, the inventors also found that the prior art processes produced low yields and were difficult to follow and produce large scale batches. Furthermore, such processes required two different protecting groups in the synthesis of the thioglycoside which then requires multiple deprotection steps. In the present process, the inventors have found that use of the bridged idopyranosyl in crystalline form and with a single protecting group (Bz) is scaled up with ease and does not require the use of multiple protecting groups which require subsequent removal. Also, in the coupling reaction of the present invention, the intermediates were solid and thus avoided the requirement of column purification and could be readily purified by crystallization methods.

The following examples are intended to further illustrate certain embodiments of the invention and are non-limiting.

Example 1-Preparation of Hypersulfated Disaccharides Having C-1 Sulfated

The compounds of the invention were prepared by the following general scheme:

Scheme of preparation of 2,5-Anhydro-3-O-(α-L-idopyranose)-D-mannitol hepta-O-sulfate sodium salt

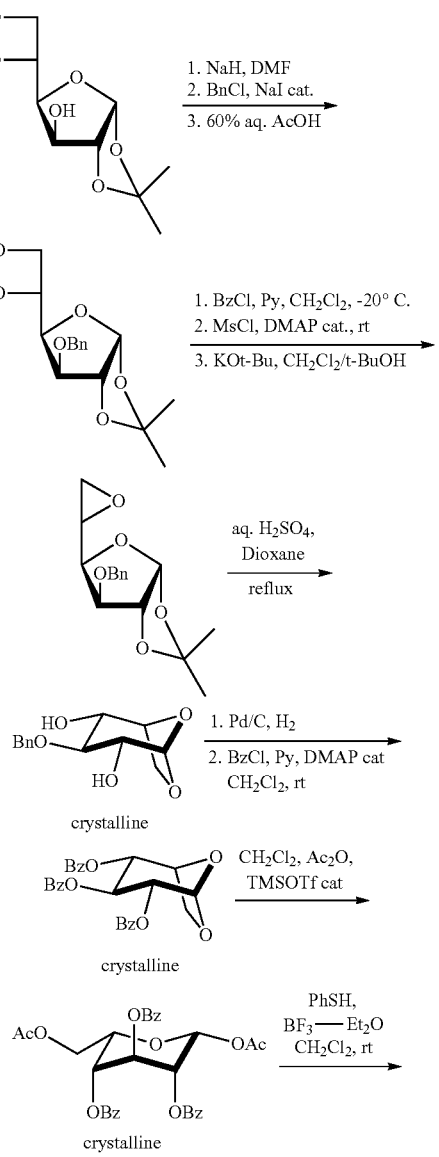

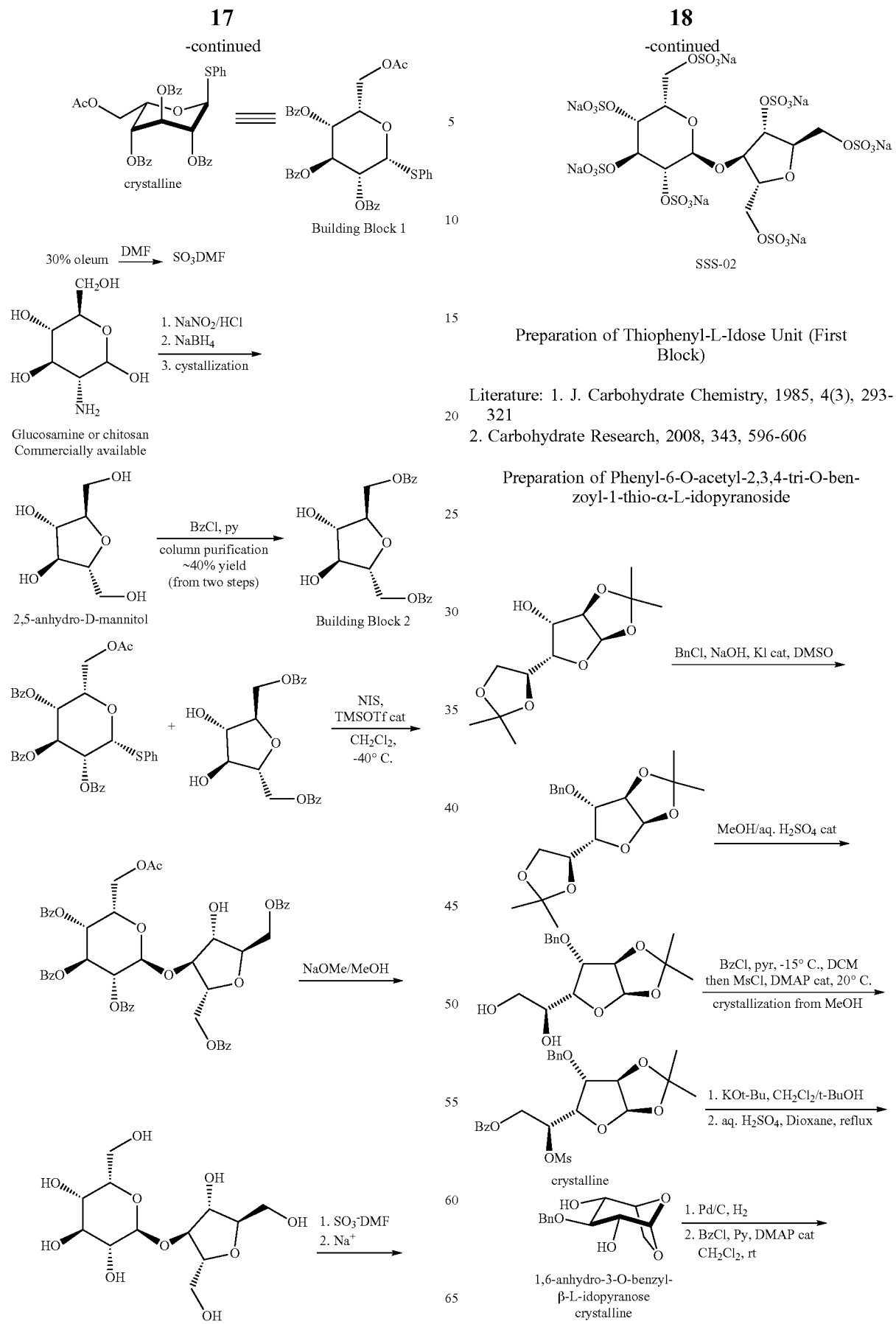
Preparation of Thiophenyl-L-Idose Unit (First Block)
Literature: 1. J. Carbohydrate Chemistry, 1985, 4(3), 293-321
2. Carbohydrate Research, 2008, 343, 596-606
Preparation of Phenyl-6-O-acetyl-2,3,4-tri-O-benzoyl-1-thio-α-L-idopyranoside

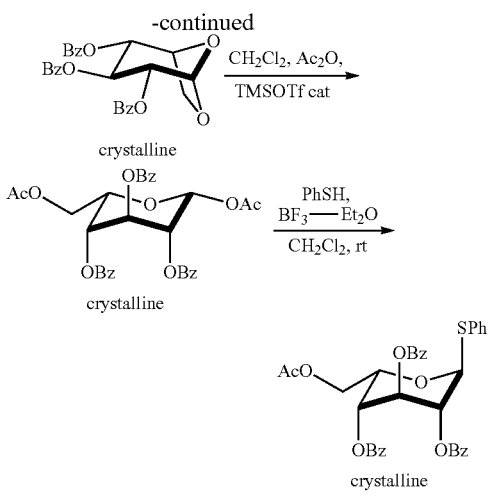

crystalline

Modified and Optimized Procedure

Diacetone-D-glucose (2.0 mol, 520.0 g) and KI (0.2 mol, 33.0 g) were dissolved in dry DMSO (1500 ml) under argon and NaOH (1.15 eq, 2.3 mol, 92.0 g) was added in one portion. After 15 min of stirring at 25° C. (almost complete dissolution), Benzyl chloride (1.05 eq, 2.1 mol, 266 g, 242 ml) was slowly added keeping reaction temperature in the range 25-35° C. Then, the reaction was stirred at 25° C. for additional 2 h (HPLC/TLC monitoring; Hep/EtOAc 1:2), poured into the mixture of Water (5 L) and MTBE (4 L) and the resulted mixture was stirred for 30 min. The phases were separated, the aqueous one was extracted with MTBE (2×700 ml) and the combined organics were washed with Water (2×800 ml) and brine (800 ml), dried over $Na_2SO_4$, filtered and evaporated under reduced pressure.

The residue (740 g) was dissolved in MeOH (3 L), a solution was cooled to 10° C. and treated with 1% aqueous $H_2SO_4$ (1 L). The reaction was stirred at 30° C. for 48-72 h (TLC control; Hep/EtOAc 1:2) and quenched by addition of solid $NaHCO_3$ (40 g). Slow gas evolution was observed. After 1 h of progressive stirring all volatiles were removed under reduced pressure and the syrupy residue was portioned between EtOAc (5 L) and Water (3 L). The phases were separated, the aqueous one was extracted with EtOAc (2×1 L) and the combined organics were washed with brine (1 L), dried over $Na_2SO_4$, filtered and evaporated under reduced pressure. The syrupy residue (650 g) which contained 90-95% of the desired 1,2-diol, contaminated with 2-5% of tetra-ol, was used without additional purification.

The crude (650 g) and dry Pyridine (6 eq, 12 mol, 970 ml) were dissolved in dry $CH_2Cl_2$ (3 L) and the solution was cooled to −25° C. A solution of Benzoyl chloride (Note 1; 1 eq, 2.0 mol, 233 ml) in dry $CH_2Cl_2$ (500 ml) was slowly added at the rate which kept the reaction temperature below −15° C. (~30 min period) and the resulted mixture was stirred for additional 2 h at −20° C. (TLC control; $CH_2Cl_2$/EtOAc 10:1). Then, Methanesulfonyl chloride (1.5 eq, 3.0 mol, 233 ml) was slowly added followed by addition of DMAP (0.2 eq, 0.4 mol, 49 g) and the reaction was heated to 20° C. and stirred for additional 12 h (TLC control). The reaction was quenched by addition of ice-water (3 L) and two-phase mixture was vigorously stirred for 30 min. The phases were separated, the aqueous one was extracted with $CH_2Cl_2$ (2 L) and the combined organics were washed subsequently with cold 2N aqueous HCl (1 L), water (500 ml) and 10% aqueous $NaHCO_3$ (500 ml), dried over $Na_2SO_4$, filtered and evaporated under reduced pressure.

The semisolid residue (~1 kg) was triturated with MeOH (4 L) at 50° C. for 1 h. The resulted suspension was then slowly cooled to 0° C., stirred for 30 min and filtered. The cake was washed with cold (2-8° C.) MeOH (2×500 ml) and Heptane (1 L), and dried under reduced pressure to give 837 g (85% yield) of Bz-Ms derivative as white solid.

Note 1:

Pivaloyl chloride (1 eq, 2.0 mol, 246 ml) may be used in the same manner instead of Benzoyl chloride to give about 80% of crude Piv-Ms derivative as semisolid A solution of Bz-Ms (507 g) in dry $CH_2Cl_2$ (3500 ml) and t-Butanol (1000 ml) was cooled to 0° C. under Argon and Potassium t-butoxide was added (247 g, 2.2 mol) by portions. The resulted mixture was stirred for 5 h at 0° C., then for 7 h at 20° C. (TLC monitoring, Heptane/EtOAc 1:1) and concentrated under reduced pressure. The residue was portioned between MTBE (2500 ml) and ice-cold water (1 L), the pH was adjusted to 7 by addition of acetic acid and the mixture was filtered through Celite. The phases were separated, the aqueous one was extracted with MTBE (1000 ml) and the combined extracts were washed with water and brine, dried over $Na_2SO_4$, filtered and concentrated under reduced pressure to give 450 g of brown oil. The residue was purified on a Silica gel (1 kg, Heptane/Ethyl acetate 10:1-4:1) to give 250 g of the desired 5,6-anhydro-L-idofuranose as yellow oil with ~90% purity by HPLC.

A solution of 3-O-Benzyl-5,6-anhydro-L-idofuranose (250 g) in 2M aqueous $H_2SO_4$ (450 ml) and 1,4-Dioxane (450 ml) was stirred under reflux for 12 h. The reaction was cooled to 10° C. and neutralized with 1 ON aqueous NaOH. The most of Dioxane was evaporated under reduced pressure, more water (1 L) was added and the aqueous mixture was extracted with EtOAc (3×800 ml). The combined organics were washed with Water and brine, dried over $Na_2SO_4$, filtered and concentrated under reduced pressure to give ~200 g of semisolid residue. The residue was crystallized from EtOH (700 ml) afforded 150 g (59% from diacetone-D-glucose) of 1,6-anhydro-3-O-benzyl-β-L-idopyranose as white solid, mp 157-158° C. (lit. 158-159° C.; JACS, 2001, 123, 3153-3154). The filtrate was concentrated to a half volume and refrigerated for 12 h to give second crop (20 g, 8%) of 1,6-anhydro-3-O-benzyl-β-L-idopyranose.

1,6-anhydro-3-O-benzyl-β-L-idopyranose (150 g, 0.6 mol) was dissolved in the mixture EtOAc/MeOH (1:1, 1200 ml) and hydrogenated over 10% Pd/C (15 g) at 50° C., 5 atm for 4 h. The mixture was cooled to 20° C., filtered through Celite and evaporated under reduced pressure. The oily residue and DMAP (22 g, 0.18 mol) were dissolved in $CH_2Cl_2$ (400 ml) and Pyridine (404 ml, 5.0 mol) and the resulted mixture was cooled to 0° C. Benzoyl chloride (276 g, 229 ml, 1.96 mol) was slowly added and the reaction was stirred for 3 h at 20° C. (TLC monitoring). The volatiles were evaporated under reduced pressure and the solid residue was portioned between EtOAc (2 L) and water (2 L). The phases were separated, the organic one was washed with cold 2N aqueous HCl (700 ml), water (500 ml) and 10% aqueous $NaHCO_3$ (500 ml), dried over $Na_2SO_4$, filtered and concentrated under reduced pressure to give ~300 g of solid residue. The residue was crystallized from Isopropanol afforded 265 g (94% yield) of the desired tribenzoate as white solid.

A solution of Tribenzoate (265 g, 0.56 mol) in $CH_2Cl_2$ (1000 ml) and Acetic anhydride (1000 ml, 10.5 mol) was cooled to 0° C. and TMSOTf (10 ml, 51.5 mmol) was slowly added. The reaction was stirred for 1 h at 0° C. (TLC monitoring), quenched by addition of $Et_3N$ (25 ml) and concentrated under reduced pressure. The solid residue was re-evaporated twice with Toluene and crystallized from Isopropanol (1200 ml) afforded 324.5 g (95% yield) of desired di-O-acetyl as white solid.

3) A solution of Di-O-acetyl (324.5 g, 0.56 mol) and Thiophenol (80.5 ml, 0.79 mol, 1.4 eq), Note 2, in $CH_2Cl_2$ (2 L) was cooled to 0° C. and $BF_3.Et_2O$ (89 ml, 0.70 mol, 1.25 eq) was slowly added. The reaction was stirred for 12 h at 20° C. (TLC monitoring) and slowly poured (gas evolution!) into 10% aqueous $NaHCO_3$ (1500 ml). After 30 min of stirring, the layers were separated; the organic one was washed with water (1 L), dried over $Na_2SO_4$, filtered and evaporated under reduced pressure. The solid residue (~350 g) was crystallized from Isopropanol afforded 300 g (85% yield) of Phenyl-6-O-acetyl-2,3,4-tri-O-benzoyl-1-thio-α-L-idopyranoside as white solid.

Note 2:
Thiocresol may be used instead of thiophenol afforded 87% of Tolyl-6-O-acetyl-2,3,4-tri-O-benzoyl-1-thio-α-L-idopyranoside as white solid Preparation of
1,6-di-O-pivaloyl-2,5-anhydro-D-mannitol (Second Block)

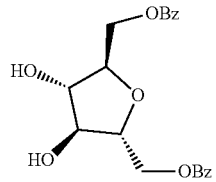

The literature known procedure was modified and applied (*Tetrahedron: Assymetry* 2000, 11, 2899-2906)

D-Glucosamine hydrochloride (400 g, 1.85 mol) was stirred in water (3000 ml) for 24 h at 25° C. to reach mutarotational equilibrium. Then, the solution was cooled to 0° C. and $NaNO_2$ (383 g, 5.6 mol, 3 eq) was added in several portion. While the stirring and keeping the temperature below 4° C. (exothermic reaction!), concentrated (37%) hydrochloric acid (315 ml, 3.7 mol) was added dropwise to form nitrous acid in situ (strongly exothermic reaction!). After additional 5 h of stirring at 0° C., the reaction was heated to 25° C. under flow of Argon in order to remove excess nitrous acid and then it was neutralized to pH 7 with 10N aqueous NaOH. The resulted solution was cooled to 0° C. and $NaBH_4$ (70.0 g, 1.85 mol) was added in small portions (gas evolution!). After 12 h of stirring at 25° C., the reaction mixture was carefully neutralized with 6N aqueous HCl and then concentrated under reduced pressure. The remaining semisolid material was treated twice with MeOH at 50° C. and the combined methanolic extracts were then concentrated under reduced pressure. The residue was extracted with Isopropanol (3×1000 ml) and the combined extracts, Note 1, were evaporated to dryness under reduced pressure to give 225 g of the crude 2,5-anhydro-D-mannitol as a yellow syrup, Note 2.

Notes
1: To remove all inorganic impurities, isopropanolic solution may be passed through ion-exchange resin columns (anionic and cationic forms)
2: According to literature, 2,5-anhydro-D-mannitol is solid and may be crystallized from EtOH or Isopropanol with seeding.

A mixture of 2,5-anhydro-D-mannitol (225 g, 1.37 mol) in dry pyridine (1000 ml) and dichloromethane (1000 ml) was cooled to −15° C. and Benzoyl chloride (366 ml, 302 ml, 2.6 mol, 1.9 eq), Note 3, was added dropwise. The reaction was stirred for 1 h at −10° C., 4 h at 0° C. and then 10 h at ambient temperature (TLC monitoring in EtOAc). All volatiles were evaporated under reduced pressure and the residue was portioned between ice-cold 3N aqueous HCl (1000 ml) and EtOAc (3000 ml). The phases were separated; the organic one was washed with water (500 ml) and brine (300 ml), dried over $Na_2SO_4$, filtered and evaporated. The residue (~550 g) was purified on a Silica gel column (3 kg, Eluent-Heptane/EtOAc from 4:1 to 1:1.5) to give 305 g (60% yield) of the desired 1,6-di-O-benzoyl-2,5-anhydro-D-mannitol as white solid and 131 g (20%) of 1,3,6-tri-O-benzoyl-2,5-anhydro-D-mannitol.

Note 3:
Pivaloyl chloride may be used instead of benzoyl chloride afforded 50% of the desired 1,6-di-O-pivaloyl-2,5-anhydro-D-mannitol together with 32% of 1,3,6-tri-O-pivaloyl-2,5-anhydro-D-mannitol.

Preparation of 2,5-Anhydro-3-O-(α-L-idopyranosyl)-D-mannitol hepta-O-sulfate Sodium Salt

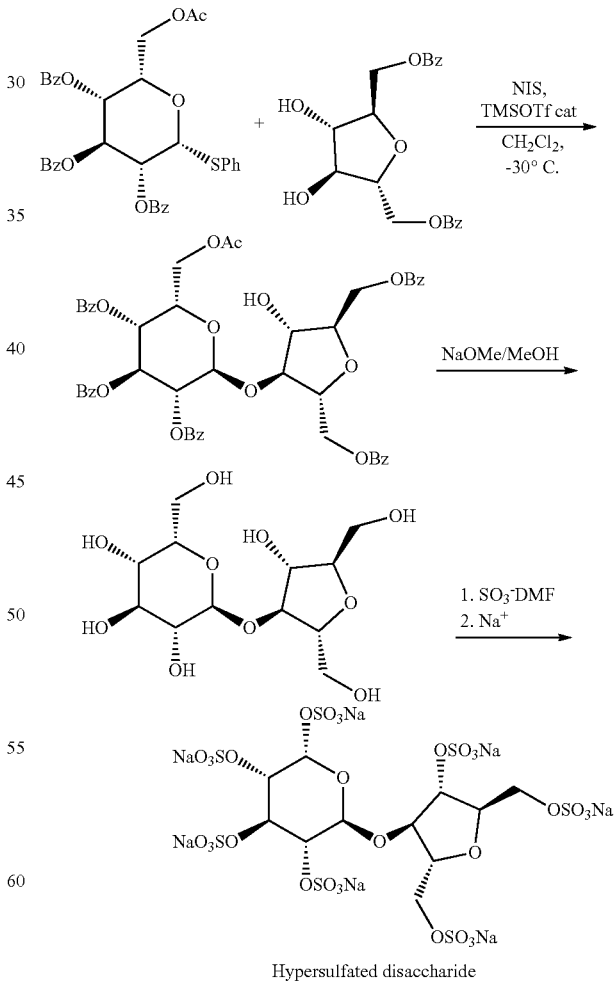

Hypersulfated disaccharide

Phenyl-6-O-acetyl-2,3,4-tri-O-benzoyl-1-thio-L-idopyranoside (125.4 g, 0.196 mol) and 1,6-di-O-benzoyl-2,5-anhydro-D-mannitol (73.0 g, 0.196 mol) were dissolved in dry $CH_2Cl_2$ (2000 ml) and the mixture was cooled to −30° C. under Argon. N-iodosuccinimide (56.2 g, 0.250 mol, 1.3 eq) was added in one portion. After 10 min of stirring, TMSOTf (5.7 ml, 29.5 mmol, 0.15 eq) was added in one portion and the reaction was stirred for additional 1 h (TLC monitoring, Heptane/EtOAc 1:1). The reaction was quenched by addition of 10% aqueous $NaHCO_3$ (50 ml) followed by 10% aqueous $Na_2SO_3$ (1300 ml) and warmed to 25° C. Then, the phases were separated, the aqueous one was extracted with $CH_2Cl_2$ (1000 ml) and the combined organics were washed Water (500 ml), dried over $Na_2SO_4$, filtered and evaporated under reduced pressure. The brown residue ('250 g) was dissolved in MeOH (900 ml) under reflux and then ~100 ml of MeOH was distilled off. The resulted mixture was cooled to 20° C., stirred for 2 h and filtered. The cake was washed with cold MeOH (2×150 ml) and Heptane (150 ml) and dried under reduced pressure afforded 148.5 g (84% yield) of the desired product as off-white solid.

The partially protected disaccharide (70.0 g, 78.4 mmol) was suspended in dry MeOH (800 ml) under Argon at 25° C. and Methanolic NaOMe (25% wt; 18.0 ml, ~78.5 mmol) was added in one portion. The reaction was stirred for 12 h at 25° C. and reaction was quenched by addition of acetic acid (7 ml). All volatiles were evaporated, the residue was triturated with EtOAc (300 ml) at 60° C. for 1 h. The mixture was cooled to 0° C., without stirring, stayed for 3 h and liquids were decanted. The solid residue was crystallized from 240 ml of the mixture MeOH/2-Isopropanol (1:2), to give after filtration and drying 20.6 g (80% yield) of the unprotected disaccharide as white solid.

A suspension of the unprotected disaccharide (20.0 g, 61.3 mmol) in dry DMF (100 ml) was cooled to −20° C. under Argon and a solution of $SO_3.DMF$ (~48%, 143 g, 0.86 mol) in dry DMF (400 ml) was slowly added at a rate that kept reaction temperature below −10° C. Thereafter the temperature was raised to 0° C., the reaction was stirred for 3 h and slowly poured (caution-gas evolution!) into the pre-cooled (0-4° C.) solution of $NaHCO_3$ (145 g) in Water (1500 ml). The resulted mixture was stirred for 20 min, neutralized with 10% aqueous $H_2SO_4$ and concentrated under reduced pressure. The solid residue was triturated with MeOH (700 ml), filtered and the solids were washed with MeOH (100 ml) and dried afforded 190 g of the desired polysulfate, contaminated with Sodium sulfate. The crude was purified (by portions of 10 g) on a Sephadex G-25 column (50-150 micron, 500 g) eluted with Water. All fractions containing the pure product were combined and evaporated under reduced pressure at 50° C. until constant weight to give 35.2 g (55% yield) of the desired heptasulfate as white powder.

The preferred product produced in this way was the hypersulfated disaccharide having seven sulfate groups in the sodium salt form as shown below (SSS-02 or SSS-056-01 or compound 2)

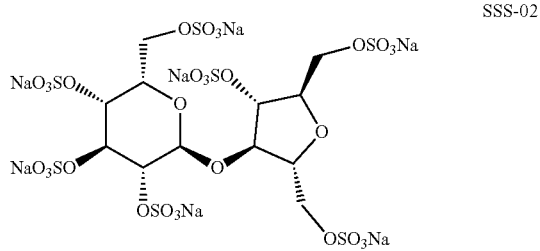

or otherwise shown as:

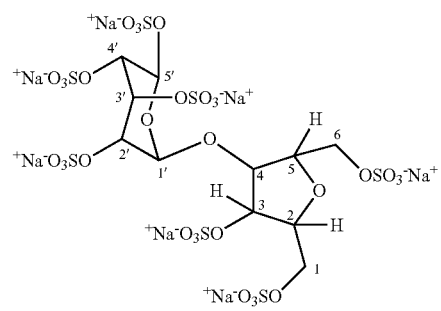

Example 2-Pulmonary Evaluation of an Animal Model (Sheep)

To illustrate the effectiveness of the formulations according to the invention to treat and alleviate allergen related diseases and conditions, including but not limited to the specific diseases and conditions recited herein, sheep were assessed in multiple experiments which compared various formulations containing no active ingredient to animals which were provided formulations comprising a compound of formula I (SSS-02). To measure pulmonary airflow resistance, the sheep were intubated with a cuffed nasotracheal tube and pulmonary airflow resistance ($R_L$) was measured by the esophageal balloon catheter technique. These methods are accepted and well known methods found in the literature.

To assess airway responsiveness, cumulative dose response curves to inhaled carbachol were performed by measuring $R_L$ before and after inhalation of buffered saline and after each administration of 10 breaths of increasing concentrations of carbachol (0.25, 0.5, 1.0, 2.0, and 4.0% wt/vol solution). Airway responsiveness was measured by determining the cumulative provocation dose ($PD_{400}$) of carbachol (in breath units) that increased $R_L$ to 400% above baseline. One breath unit was defined as one breath of 1% carbachol solution.

For airway studies, each animal's baseline airway responsiveness ($PD_{400}$) was determined and then, on different experimental days, the test sheep underwent airway challenge with *Ascaris suum* antigen. $R_L$ was measured to establish baseline, then measured again immediately after antigen challenge and hourly for an eight hour period and then a post challenge $PD_{400}$ was measured 24 hours after antigen challenge. In each of the Figures presented herein, FIGS. 1A, 2A, 3A etc. present day two data measured on an hourly basis for the eight hour period and contain control data (closed circles) and drug treatment data (open circles or triangles (closed or open)). The drug treatment experiments were conducted on the same animals used in the control studies but after a period of several weeks following the day 3 $PD_{400}$ measurements. FIGS. 1B, 2B, 3B etc. contain the day one baseline $PD_{400}$ data and day three $PD_{400}$ data following antigen challenge in control or drug treated animals.

Data were expressed or may be expressed as (a) mean+/− SE % change of $R_L$ and (b) $PD_{400}$ in breath units. Data were also expressed as (c) % protection of Early Airway Response (EAR, for 0-4 hours) and Late Airway Response (LAR, for 4-8 hours), as estimated by area under the curve for EAR and LAR respectively. And (d) AHR %

$$\text{protection} = 100 - \frac{\text{Baseline } PD_{400} - drug_{antigen}PD_{400}}{\text{Baseline } PD_{400} - Control_{antigen}PD_{400}} \times 100$$

Thus, the numbers in the Figures as presented were obtained by the formula:

Baseline $PD_{400}$-drug$_{antigen}PD_{400}$ was $x$-$y$;Baseline $PD_{400}$-Control$_{antigen}PD400$ was $x$-$z$. $x$-$y$/$x$-$z$× 100=$n$. 100−$n$=$X$ % protection in $AHR$.

In the studies presented in FIGS. 1A-9B, the data shows the % change in $R_L$ and $PD_{400}$ in breath units for Control antigen response studies and for Drug-Treated antigen response studies.

FIG. 1A shows a graph comparing the percentage change in pulmonary airflow resistance (measured as cm $H_2O$/L/sec) (i.e., the $R_L$) following the indicated time after antigen administration (time=0) of sheep's responses (n=5) to exposure to antigen only (closed circles) (control) and antigen plus a liquid oral dosage of 0.5 mg/kg×4 days (QD) of the heptasulfated disaccharide (sodium salt) designated as SSS-056-01*. The last dose was administered ninety minutes before antigen challenge (i.e., −1.5 hr). Data are shown as antigen-induced mean plus or minus SE % change in $R_L$ in sheep (n=5) exposed to antigen first with no drug and then again several weeks later with antigen plus SSS-056-01.

FIG. 1B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment (90 minutes beforehand) with an oral dose of SSS-056-01 (0.5 mg/kg×4 days (QD)) in liquid form. $PD_{400}$ is defined as the provocating dose of carbochol in breath units which caused a 400% increase in $R_L$. One breath unit is one breath of 1% solution of carbochol. $PD_{400}$ is an indicator of airway responsiveness. The 0.5 mg/kg oral dose (QD for 4 days) inhibited EAR by 77%, LAR by 95% and AHR by 100%.

FIG. 2A shows a graph comparing the percentage change in pulmonary airflow resistance (i.e., the $R_L$) following the indicated time after antigen administration (time=0) of sheep's responses (n=5) to exposure to antigen only (closed circles) (control) and antigen plus an iv dose (0.5 mgs/kg×4 days (QD) of the heptasulfated disaccharide designated as SSS-056-01 (open circles). The last does was administered 90 minutes before antigen challenge (i.e., 1.5 hrs) Data are shown as antigen-induced mean plus or minus SE % change in $R_L$ in sheep (n=5) exposed to antigen first with no drug and then again several weeks later with antigen plus SSS-056-01. The results show that there is no difference in bioavailability between the intravenous administered dose and the oral dose shown in FIG. 1A administered once a day.

FIG. 2B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment (1.5 hours) with an i.v. Dose (0.5 mgs/kg×4 days (QD)) of SSS-056-01. The results again show that there is no difference between the i.v. route of administration (bioavailability) and the oral route shown in FIG. 1B. The 0.5 mg/kg i.v. dose (QD for 4 days) inhibited EAR by 77%, LAR by 92% and AHR by 100%.

FIG. 3A shows a dose-response graph comparing the percentage change in pulmonary airflow resistance (measured as cm $H_2O$/L/sec) (i.e., the $R_L$) following the indicated time after antigen administration (time=0) of sheep's responses (n=5) to exposure to antigen only (closed circles) (control) and antigen plus a liquid oral dosage at various strengths (0.25 mg/kg (open circles); 0.5 mg/kg (closed triangles) and 1 mg/kg (open triangles)) of the heptasulfated disaccharide designated SSS-056-01 (open circles). Data are shown as antigen-induced mean plus or minus SE % change in $R_L$ in sheep (n=5) exposed to antigen first with no drug and then again several weeks later with antigen after being pretreated with various oral doses of SSS-056-01 administered 90 min before antigen challenge.

FIG. 3B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pre-treatment with various oral doses of SSS-056-01 (0.25, 0.5 and 1.0 mgs/kg) administered 90 min. before the antigen challenge. +P<0.05 vs. baseline; and *P<0.05 vs. antigen control. The data in FIGS. 3A and 3B demonstrate that a single oral dose of SSS-056-01 at 0.25 mg/kg was ineffective while 0.5 mg/kg and 1 mg/kg inhibited LAR (71% and 77% inhibition) and AHR (100% inhibition) without an effect on EAR.

FIG. 4A shows a graph comparing the percentage change in pulmonary airflow resistance (measured as cm $H_2O$/L/sec) (i.e., the $R_L$) following the indicated time after antigen administration (time=0) of sheep's responses (n=8) to exposure to antigen only (control, closed circles), and antigen plus multiple (3× total; 1× every 12 hours) liquid oral doses of 0.25 mg/kg, 0.5 mg/kg and 1.0 mg/kg of the heptasulfated disaccharide designated as SSS-056-01 (open circles, closed triangle, open triangles respectively; three weeks apart). Data are shown as antigen-induced mean plus or minus SE % change in $R_L$ in sheep (n=8) exposed to antigen first with no drug and then again several weeks later with antigen after being pretreated before antigen exposure with 0.25 mg/kg, 0.5 mg/kg and 1.0 mg/kg SSS-056-01 (1× each 12 hr period, 3 weeks apart). Antigen challenge was ninety minutes after the last dose.

FIG. 4B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=8) exposed to antigen first with no drug and then again with antigen several weeks later following pre-treatment before exposure with a liquid oral dose of SSS-056-01 (0.25 mg/kg, 0.5 mg/kg and 1.0 mgs/kg; 3 weeks apart) administered 1×3 each 12 hours. Antigen challenge was ninety minutes after the last mg/kg dose. The results show that the effect of multi-dose oral SSS-056-01 is cumulative. While 0.25 mg/kg×3 doses is ineffective; 0.5 mgs/kg×3 and 1 mg/kg×3 inhibited EAR (30% and 54% inhibition), LAR (85% and 87% inhibition) and AHR (100% inhibition). 1 mg/kg caused significantly greater inhibition of EAR than 0.5 mg/kg while the effect on LAR and AHR were comparable.

FIG. 5A shows the area under the curve for early phase (AUC-EAR$_{0-4\ hr}$) from the data obtained in FIG. 4A.

FIG. 5B shows the area under the curve for the late phase (AUC-LAR$_{4-8\ hr}$) from the data obtain in FIG. 4A.

FIG. 6A shows a graph comparing the percentage change in pulmonary airflow resistance (measured as cm $H_2O/L/$sec) (i.e., the $R_L$) following the indicated time after antigen administration (time=0) of sheep's responses (n=5) to exposure to antigen only (closed circles) (control) and antigen plus a liquid oral dosage of 0.5 mg/kg administered twice a day (BID) for a total of seven doses of the heptasulfated disaccharide designated as SSS-056-01 (open circles). Data shown are antigen-induced mean plus or minus SE % change in $R_L$ in sheep (n=5) exposed to antigen first with no drug and then again several weeks later with antigen after being pretreated before antigen exposure with the seven doses. The last dose was administered 90 minutes before the antigen challenge.

FIG. 6B shows a bar graph illustrating the effect of pretreatment on airway hyperresponsiveness (AHR) in allergic sheep. Data are shown as mean plus or minus SE $PD_{400}$ (airway responsiveness) in breath units at baseline, 24 hours post-antigen challenge in a group of sheep (n=5) exposed to antigen first with no drug and then again with antigen several weeks later following pretreatment with seven total doses administered every 12 hours before exposure with an oral dose of SSS-056-01 (0.5 mg/kg). Antigen exposure occurred ninety minutes after the last 0.5 mg/kg treatment. The data in FIGS. 6A and 6B show that the effect of multidose BID dosing of oral SSS-056-01 is cumulative. 0.5 mg/kg oral doses (BID×7 doses) inhibited EAR by 76%, LAR by 96% and AHR by 100%. This is significantly better than 0.5 mg/kg×3 doses. BID dosing (×7) is comparable to QD (×4) dosing.

FIG. 7A shows the effect of multi-dose oral SSS-056 on antigen-induced EAR, LAR and AHR in sheep (QD dosing). Oral SSS-056-01 (0.5 mg/kg) was administered once daily in the morning×4 days, and antigen challenge was performed 90 minutes after the last dose (n=5). EAR and LAR are shown as antigen-induced % change in $R_L$±SE, without (control, closed circles) and after treatment with oral SSS-056-01 (open circules). The results also show that the effect of multi-dose oral SSS-056-01, BID versus QD dosing is comparable.

FIG. 7B shows post-antigen AHR shown as mean±SE $PD_{400}$ for the baseline and 24 hours post-antigen without (control) and after treatment with SSS-056-01. +P<0.05 vs. Baseline; *P<0.05 vs. antigen control.

*This compound is also described herein as SSS-02.

FIG. 8A shows the effect of single dose "inhaled" SSS-056 on antigen-induced EAR, LAR and AHR in sheep (n=5). Inhaled SSS-056-01 in bacteriostatic injection water was administered 30 minutes before antigen challenge. EAR and LAR are shown as antigen-induced % change in $R_L$±SE without (control) and after treatment with various doses of SSS-056-01.

FIG. 8B shows post antigen AHR shown as mean+/−SE $PD_{400}$ for the baseline and 24 hour post-antigen, with (control) and after treatment with 5 mg and 10 mg inhaled SSS-056-01. This shows that 10 mg single dose of inhaled SSS-056-01 inhibits LAR (75% inhibition) and AHR (100% inhibition) without an effect on EAR; while the 5 mg dose was ineffective.

FIG. 9A shows multi-dose inhaled SSS-056-01 (10 mg×3) had no cumulative effect on EAR (n=6), but did have an effect on LAR. The data was comparable to a single dose, as shown in FIG. 8.

FIG. 9B shows post antigen AHR shown as mean SE $PD_{400}$ for the baseline and 24 hour post-antigen, with (control) and after treatment with 10 mg×3 inhaled SSS-056-01. This shows that multiple dose (10 mg×3) of inhaled SSS-056-01 inhibits LAR (75% inhibition) and AHR (100% inhibition) without an effect on EAR FIG. 10 shows the proton NMR of SSS-056-01 (2,5-anhydro-3-O-(α-L-idopyranose)-D-mannitol-hepta-O-sulfate-hepta sodium salt).

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize or be able to ascertain using no more than routine experimentation, numerous embodiments of the claimed invention which may not have been expressly described. Such embodiments are within the scope of the invention.

What is claimed is:

1. A process for producing a compound of formula I

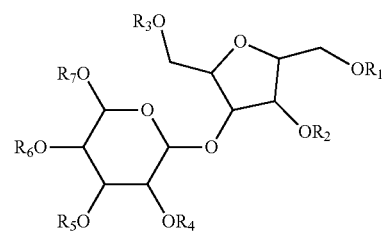

wherein $R_1$-$R_7$ are independently selected from the group consisting of $SO_3H$ or $PO_4H$,
comprising the steps of (1) reacting a thioglycoside of formula Ia with a mannitol of formula Ib to form a compound of formula Ic;

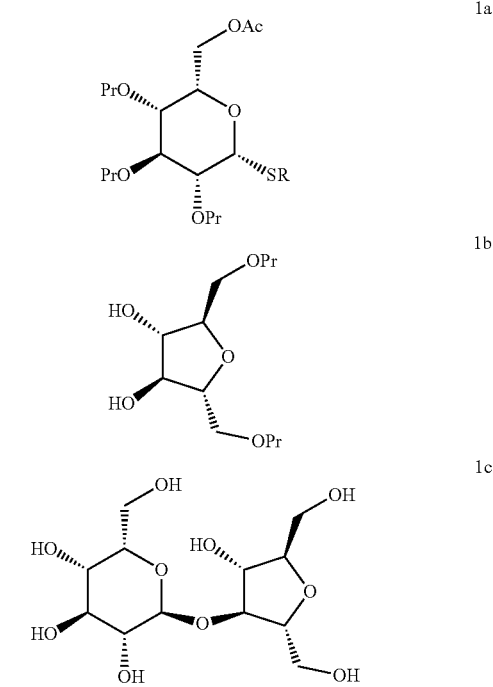

wherein R is Ph; and Pr is Bz;

(2) reacting the compound of formula Ic with a sulfating reagent to form a compound of formula I and wherein the thioglycoside Ia is produced using 1,6-anhydro-3-O-benzyl-βL-idopyranose (3)

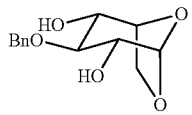

3 as an intermediate in the process to make a compound of formula I.

2. The process according to claim 1 wherein the compound of formula Ia is produced by a process which comprises (a) reacting 1,6-anhydro-3-O-benzyl-β-L-idopyranose (3)

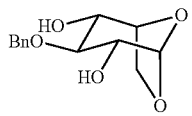

3 with a reducing agent and benzoyl chloride to form compound 4:

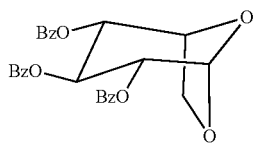

4

(b) reacting compound 4 with an acetylating agent to form compound 5:

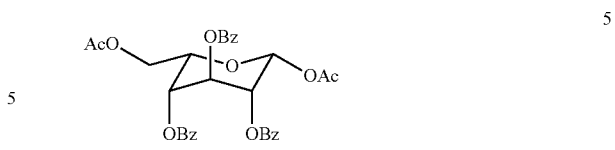

5

(c) thiolating compound 5 with a thiolating reagent to form a compound of formula Ia.

3. The process according to claim 2 wherein pivaolyl chloride is used as a reagent in place of beyzoyl chloride to form compound 4'

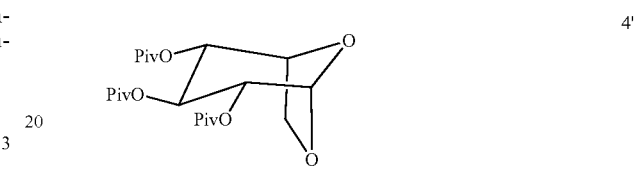

4' and compound 4' is acetylated to form compound 5'

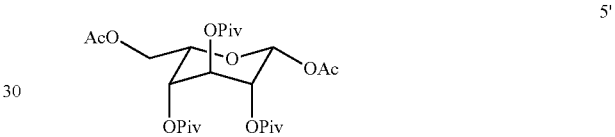

5' which is further reacted with a thiolating reagent to form the pivolated version of a crystalline form of compound Ia.

4. The process according to claim 3 wherein the thiolating reagent is selected from thiophenol or thiocresol.

* * * * *